(12) United States Patent
Hoyt

(10) Patent No.: US 6,455,861 B1
(45) Date of Patent: *Sep. 24, 2002

(54) FLUORESCENCE POLARIZATION ASSAY SYSTEM AND METHOD

(75) Inventor: Clifford C. Hoyt, Needham, MA (US)

(73) Assignee: Cambridge Research & Instrumentation, Inc., Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/395,661

(22) Filed: Sep. 14, 1999

Related U.S. Application Data

(60) Provisional application No. 60/109,618, filed on Nov. 24, 1998.

(51) Int. Cl.[7] .............................................. G01N 21/64
(52) U.S. Cl. .................................... 250/458.1; 356/318
(58) Field of Search ........................... 250/458.1, 459.1, 250/461.1, 462.2, 252.1 R; 356/318, 417, 317

(56) References Cited

U.S. PATENT DOCUMENTS

| | | | | |
|---|---|---|---|---|
| 3,940,748 A | * | 2/1976 | Carson ................. 340/173 CC |
| 4,555,177 A | * | 11/1985 | Barrett ...................... 356/318 |
| 4,962,493 A | * | 10/1990 | Kramer et al. ........... 369/44.11 |
| 5,051,162 A | * | 9/1991 | Kambara et al. ............ 204/249 |
| 5,424,841 A | * | 6/1995 | Van Gelden et al. ....... 356/417 |
| 5,672,880 A | | 9/1997 | Kain ....................... 250/458.1 |
| 5,719,391 A | | 2/1998 | Kain .......................... 250/235 |
| 5,943,129 A | * | 8/1999 | Hoyt et al. ................. 356/318 |
| 6,005,709 A | * | 12/1999 | Silver ......................... 359/368 |
| 6,229,635 B1 | | 5/2001 | Wulf |

OTHER PUBLICATIONS

Fluorescence Polarization and Anisotropy in High Throughput Screening: Perspectives and Primer, Journal of Biomolecular Screening, vol. 5, No. 5, 2000, pp. 297–306.

* cited by examiner

*Primary Examiner*—Georgia Epps
*Assistant Examiner*—Richard Hanig

(57) ABSTRACT

An instrument is disclosed for fluorescence assays which is capable of reading many independent samples at the same time. This instrument provides enhanced throughput relative to single-sample instruments, and is well-suited to use in general fluorescence, time-resolved fluorescence, multi-band fluorescence, fluorescence resonance energy transfer (FRET), and fluorescence polarization. This invention is beneficial in applications such as high-throughput drug screening, and automated clinical testing. Also disclosed are means and methods for a fluorescence polarization measurement which is highly sensitive, inherently self-calibrated, and unaffected by lamp flicker or photobleaching. This fluorescence polarization invention can be practiced on a variety of fluorescence instruments, including prior-art equipment such as microscopes and multi-well plate readers.

60 Claims, 14 Drawing Sheets

FLUORESCENCE POLARIZATION ASSAY SYSTEM AND METHOD

RELATED APPLICATIONS

This application claims priority from U.S. Provisional Patent Application Ser. No. 60/109,618 which was filed on Nov. 24, 1998.

BACKGROUND OF THE INVENTION

1. Field of the Invention

The present invention relates to equipment and methods for assaying the amount of optical fluorescence, and the degree of fluorescence polarization, in samples.

2. Background and Description of the Related Art

Fluorescence Methods and Terminology.

Fluorescence involves exciting a molecular group with light of a first wavelength, causing it subsequently to emit light of a second, longer wavelength. The molecular group is termed a fluorophore, and the first and second types of light are termed "excitation" and "emission" light, respectively. Between excitation and emission, the molecular group is said to be in an excited state. Depending on the molecular group involved, the time spent in the excited state can vary widely, from a few nanoseconds to several microseconds. The duration of the excited state is termed the fluorescence lifetime. It is common to chemically engineer a fluorescent marker compound by grafting a fluorophore to a chemical group that reacts only or primarily with a very specific target molecule. The resultant fluorescent marker will bind only to very specific targets, and has fluorescence properties of the fluorophore.

Fluorescent markers are used to disclose the presence and/or location of targets within a sample, which may contain a variety of other compounds. For reliable detection, the other compounds in the sample must exhibit a very low degree of fluorescence, or there must be a way to discriminate between fluorescence emission resulting from the target compound and that from other compounds in the sample. Since the mechanism of fluorescence is present to at least some degree in most compounds, discrimination means are usually employed. Among the means are discrimination by wavelength of excitation light, by wavelength of emission light, and by fluorescence lifetime. Typically, discrimination by excitation wavelength involves making measurements using excitation light that has been filtered to contain light of only a selected wavelength band. Similarly, measurement of emission light through a filter that admits only a selected wavelength band provides a means to discriminate by emission wavelength.

Fluorescence lifetime discrimination is performed by a variety of methods, the simplest of which is to excite using a modulated source, and to observe emission using synchronous detection methods. For example, a target compound with a long fluorescence lifetime may be detected by exciting the sample with brief pulses, while measuring emission using a gated detector which is insensitive for a controlled, brief interval after excitation. Such a detector will not respond to compounds having a short fluorescence lifetime, which will have ceased emission by the time the detector becomes responsive. However, the target species, having a long fluorescence lifetime, will continue to emit for considerably longer, and the majority of its emission will be detected. Alternative approaches can also be used with single-element detectors, including detection with lock-in amplifiers, quadrature detection, and other standard signal analysis techniques. Imaging detection is possible with a gated intensifier or microchannel plate (MCP), by electronic shuttering, or by pixel shifting between photosensitive and non-photosensitive regions of a CCD detector.

Discrimination by these means is useful for removing so-called 'background' fluorescence arising from optical components, solvents, culture dishes, and the like, which are necessary elements in a fluorescence experiment but whose fluorescence signal is not seen as contributing meaningful information. That is, these are means for removing unwanted contaminant signals and for obtaining an enhanced signal-to-noise ratio in the sample fluorescence measurement.

It is possible to use discrimination techniques not just to remove background, but to learn more about the sample itself. For example, two or more fluorescent markers can be used which have distinct excitation or emission properties, so a single sample can be tagged with multiple markers to identify different structures or entities. The fluorescent signals are then resolved to obtain information about each marker independently. This technique is often termed multiprobe fluorescence.

Discrimination by excitation or emission wavelength may also be used to learn additional information about a single target species. For some fluorescent markers, the characteristic wavelengths of optimal excitation or emission vary with the chemical properties of the environment, such as the pH, salinity, concentration of calcium, or the presence of other, very specific molecules. Observing how fluorescence intensity varies with excitation wavelength, or measuring the spectrum of emission light, can provide a measurement of the chemical environment of the fluorescent marker. These practices are termed fluorescence excitation spectroscopy and fluorescence emission spectroscopy.

One case of special significance is fluorescence resonance energy transfer (FRET), which employs two molecular groups having carefully related properties. Typically, one group contains a fluorophore that is characteristically excited at a first wavelength and emits at a second wavelength. The other group is characteristically excited at the second wavelength and emits at a third wavelength. Depending on the presence, concentration, or molecular conformation of the two groups, the likelihood of interaction between the two groups is higher or lower. When the likelihood of interaction is high, energy is transferred from excited molecules in the first molecular group to the second molecular group, resulting in emission light at the third wavelength. Thus, sample emission at the third wavelength is enhanced and emission at the second wavelength is depressed, compared to the case when the likelihood of interaction is low. Typically, a FRET experiment involves excitation at the first wavelength while monitoring the level of emission at the second and third wavelength bands. From the ratio of emission at these bands, the level of interaction is inferred.

Additional information can be obtained in some cases by analyzing the fluorescence polarization (FP), which involves exciting the sample with linearly polarized light and measuring the degree of linear polarization in the emission light. Excitation light preferentially excites those molecules having a selected geometrical orientation relative to the light's polarization vector. Thus, the population of excited molecules is selectively oriented, rather than randomly so, at the time of excitation. If the fluorescence lifetime is comparable to or shorter than the molecular reorientation time, then the molecules will also be preferentially oriented when they emit, and the emission light will be linearly polarized to some degree. By measuring the degree of polarization, one infers the degree of preferential orientation at time of emission. It is conventional to refer to the degree of polarization (DOP) in terms of millipolarization units (MPU), defined as $$DOP=1000*(I_{\|}-I_{195})/(I_{\|}+I_{\perp})  \quad [1]$$

where $I_{\|}$ and $I_{\perp}$ are the intensities of fluorescence emission polarized in the same sense as the excitation light and polarized orthogonal to it, respectively. Related measures are also used to quantify fluorescence polarization, based on substantially the same information.

Many factors can affect molecular re-orientation time, including rotational viscosity, temperature, and whether the fluorescent molecule is bound to another molecule or not. Measurement of fluorescence polarization (FP) is often used as a way to assess whether a molecule is in its bound or free state.

Equipment used in Fluorescence Instruments

It is common to use mercury or xenon arc lamps with optical filters for fluorescence excitation. These are very useful for providing ultraviolet (UV) light, which some fluorophores require. When only visible light is required for excitation, a less expensive tungsten lamp can be used instead. Most often, lamp sources are used when fine definition of the illumination region is not required, or when a large region is to be illuminated. Laser sources are sometimes employed to illuminate small, well-defined regions, because of their higher specific radiance and more readily controlled beam properties. For example, lasers are often used as excitation sources in confocal equipment, and to create very high flux densities in e.g. single-molecule detection experiments. They are limited in that they emit a restricted, often discrete set of wavelengths in contrast to lamps, which generally produce a continuous spectrum that can be filtered to provide any desired band within a range.

Detection of fluorescence in multiple-sample assay plates is typically performed by optical scanning means, by sequential measurements with single-element instruments that are mechanically stepped across the individual sample regions, or by use of array detectors with flood-light sources,. Examples of optical scanning means include Kain, in U.S. Pat. Nos. 5,672,880 and 5,719,391, where a galvo-driven scanning mirror directs excitation light toward, and emission light from, one of a plurality of samples. This allows a single lamp and a single detector to be used, and minimizes the number of moving parts required.

In systems such as the Analyst from LJL Biosystems (Sunnyvale, Calif.), a single-element reader is mechanically stepped across the various samples in a sample plate. The Analyst arrangement enables use of a specialized optical design where the excitation and emission optics define a sample volume in an approximately confocal arrangement, with different optical axes angles. However, readout time and instrument cost are increased because of the need for mechanical stepping.

These approaches use a single excitation source and a single detector when measuring total fluorescence levels. Typical detector types include avalanche photodiodes (APD), photomultiplier tubes (PMT), or other devices capable of operating at low light levels. This is important, as high sensitivity is vital to fluorescence assay instruments. And since only a single detector is required, the cost or complexity of that element can be increased somewhat without great consequence.

In contrast, other systems use an array detector such as a silicon charge-coupled device (CCD) or photodiode array to measure fluorescence from many samples at once. This parallelism increases the instrument throughput, and because modem CCD detectors have low-noise readout circuitry, the detector does not impose a significant penalty in terms of reduced sensitivity. The Arthur system from E.G.&G. Wallac (Gaithersburg, Md.) utilizes a flood source to illuminate many samples at once, and a CCD sensor to measure the fluorescence emission.

Fluorescence Polarization Considerations

For FP analysis, additional components are employed. It is necessary to polarize the excitation source, which is readily achieved with conventional polarization optical elements for the visible and UV, such as dichroic sheet polarizer, polarizing beamsplitter cubes, and crystal polarizers such as Glan-Taylor or Rochon prisms.

The polarization state of the emission light is analyzed using one of several approaches. In one class of FP instruments, emission light is analyzed using a linear polarizer that is rotated to two orthogonal settings while a detector is read, to measure the components $I_{\|}$ and $I_{\perp}$. Typically a sheet dichroic type of polarizer is used, but use of any linear polarizer would result in a similar overall function. This type of instrument, referred to in the present application as a sequential-measurement FP reader, has a number of drawbacks. Because it measures the two states in time-sequence rather than simultaneously, its accuracy is degraded by fluctuations in the lamp or laser source. One can employ a reference detector to monitor the source fluctuations, and numerically compensate for variations by e.g. division, but this approach is not entirely successful. Further, intrinsic changes in the sample during the process of measurement, such as the effects of photobleaching, cannot be corrected. Finally, mechanical moving parts are normally used to select alternating polarization states, introducing reliability concerns.

Another class of FP instruments uses a polarizing beamsplitter (PBS). This separates the fluorescent emissions into two distinct beams according to their polarization state, and these beams are directed onto separate detectors to measure the components $I_{\|}$ and $I_{\perp}$. This type of instrument is termed a simultaneous-measurement FP reader in the present application. It measures both states simultaneously, and so does not suffer the problems of the sequential-measurement FP reader just described. However, it has other limitations. A PBS is a pair of right-triangle prisms with optical coatings on the hypotenuse, at which face they are cemented or joined to form a cube. This means that the two detectors must be physically distinct parts, rather than being two segments of a multi-element detector, because the images formed by the two beams are not coplanar. The need for two detectors, two sets of readout circuitry, and sometimes two lenses, means increased cost and complexity.

Both of the FP instrument designs described above read a single sample at a time, and no known commercial FP instrument can read a plurality of samples at once. This is a weakness for applications such as clinical testing and high-throughput drug screening, since single-sample systems inevitably have lower sample throughput. While one can conceive of an instrument based upon an array of detectors, polarizers, and sources, the construction of an instrument with competitive price and performance to existing single-sample instruments has not been achieved. This is a significant limitation of the prior-art designs. A system described in U.S. Pat. No. 5,943,129 to Hoyt and Miller could be used for detection of multiple samples within an assay plate, and can select alternating polarization states using liquid crystal elements means rather than mechanical means. However, it is a sequential-measurement FP reader with all the inherent problems of this approach, as explained above.

Another inherent limitation of all prior-art systems is their need for calibration. There is generally some polarization dependence in the transmission of lenses, in the reflection from mirrors, and the like. So, the amount of light reaching the detector(s) is altered by these elements, which are normally present in a practical system. For a simultaneous-reading PBS-type instrument, this is compounded by the fact that the two detectors employed generally have somewhat different quantum efficiencies, and are measured by different electronic circuits. Due to the differences in the optical elements when transmitting the two types of polarized light, and possible detector differences, the system has different responsivity for measurement of $I_\parallel$ and of $I_\perp$. Since there is no way to assess the relative proportions of $I_\parallel$ and $I_\perp$, this voids the measurement of FP unless the system can be calibrated.

The factors producing disparate responsivity between $I_\parallel$ and $I_\perp$ are not necessarily constant in time, nor are they the same at all wavelengths. Consequently, calibration must be undertaken separately for each wavelength band of fluorescent emission, and must be repeated at intervals to accommodate aging in components and circuitry. These problems are most severe when two detectors are used, as in a simultaneous measuring system.

In summary, the aforementioned art includes fluorescence measurement instrumentation for optically scanning a plurality of samples on a plate, or mechanically stepping a single-point system to a plurality of samples, or for flood-illuminating a plate and imaging a plurality of samples using a CCD detector. It provides methods for measuring the degree of fluorescence polarization through simultaneous-measurement or time-sequential measurement of orthogonally polarized emission components, but all suffer from significant limitations. All require calibration to obtain high-accuracy readings. Those which employ simultaneous-measurement of orthogonally polarized fluxes have higher cost and parts count, while those employing sequential-measurements often require moving parts; they are sensitive to fluctuations in the lamp or laser used to excite fluorescence; and their accuracy can be compromised by the inevitable photobleaching of the sample itself. Nor does any prior art system enable measuring the fluorescence polarization of many samples at once. Thus, no prior art system provides a self-calibrated measurement of fluorescence polarization, with high accuracy and the capability to measure many samples at once, for reading multiwell plates, microscope slide samples, and similar applications.

SUMMARY OF THE INVENTION

It is an object of the present invention to describe a means for measuring fluorescence which can read many samples at once, in parallel, for high throughput screening. A further object is to enable reading plates, pipettes, tubes, microscope slides, and a wide variety of formats with little or no change to the instrument hardware. Another object is to provide for measurement of multi-band fluorescence, time-resolved fluorescence, fluorescence emission spectroscopy, and fluorescence excitation spectroscopy in a single instrument. A further object is to provide enhanced sensitivity measurements, to enable use of smaller sample sizes and lower concentrations. Yet another object is to provide a method and means for fluorescence polarization measurements which are inherently accurate with no need for calibration, and which do not suffer degraded accuracy despite fluctuations in the excitation source. A final object is to provide means and methods for improving the accuracy and sensitivity of fluorescence polarization measurements made with existing fluorescence instrumentation.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

The present invention provides for a fluorescence measurement instrument comprising excitation means, a plurality of sample regions, and detection means; where the excitation means produce a first beam and a diffractive optical beamsplitter element that splits the first beam into plural secondary beams; the plural secondary beams excite the plurality of sample regions simultaneously to effect fluorescence; and the detection means detect the fluorescence from the plurality of sample regions.

The present invention further provides for a fluorescence measurement instrument comprising excitation means, a sample region, and detection means; where the excitation means and the detection means comprise an objective and a photodetector; where light from the laser source is directed toward the sample region by a mirror located between the sample region and the objective.

The present invention additionally provides for a fluorescence polarization measurement instrument comprising excitation means, at least one sample region, and detection means; where the excitation means produce light that is substantially linearly polarized along a first axis of polarization at the sample region; where the detection means comprise an objective, a photodetector, and a polarization analyzer; where the photodetector provides a plurality of spatially distinct pixel regions; where the objective directs a beam of fluorescent light from the sample toward the polarizing beamsplitter; where the polarization analyzer divides the beam of fluorescent light into two linearly polarized secondary beams, one with polarization axis oriented substantially parallel to the first axis of polarization and the other with polarization axis oriented substantially perpendicular to the first axis of polarization; and where the secondary beams of fluorescent light are directed onto the spatially distinct pixel regions of the photodetector by the polarization analyzer.

Another embodiment of the present invention is a fluorescence polarization measurement instrument comprising excitation means, at least one sample region, and a detection means; where the excitation means produce light that is directed at the sample region to effect fluorescent emission and that is substantially linearly polarized along a first axis of polarization at the sample region; where the detection means comprise an objective, a plurality of independent detector regions, and a polarization analyzer; where the plurality of independent detector regions comprises one of a unitary detector with multiple pixel regions and multiple detectors; where the objective collects the fluorescent emission from the sample region and directs the fluorescent emission in a beam toward the polarization analyzer; where the polarization analyzer divides the beam of fluorescent emission into two linearly polarized secondary beams, one with polarization axis oriented substantially parallel to the first axis of polarization and the other with polarization axis oriented substantially perpendicular to the first axis of polarization; where the linearly polarized secondary beams are directed by the analyzer to separate detector regions; where said excitation means further provide switching means for changing the state of polarization of the excitation light at the sample region during a single fluorescence polarization measurement from a first orientation parallel to the first axis of polarization to a second orientation parallel to a second axis of polarization which is substantially perpendicular to the first axis of polarization.

Finally, the present invention provides for a method of measuring fluorescence polarization, consisting of illuminating a sample to effect fluorescence emission with a beam of excitation light that is linearly polarized along a first axis measuring the intensities of a first component of the fluorescence emission that is polarized along the first axis and a second component of the fluorescence emission that is polarized orthogonal to the first axis while the sample is illuminated with the beam of excitation light that is linearly polarized along the first axis; switching the state of polarization of the beam of excitation light to be linearly polarized along a second axis substantially orthogonal to the first axis; measuring the intensities of a third component of fluorescence emission that is polarized along the first axis and a fourth component that is polarized orthogonal to the first axis while the sample is illuminated with the beam that is linearly polarized along the second axis; calculating the fluorescence polarization based on the measurements of the intensities of the first, second, third and fourth components.

BRIEF DESCRIPTION OF THE DRAWINGS

In the drawings, wherein like reference numerals denote similar elements throughout the several views.

DETAILED DESCRIPTION OF THE PRESENTLY PREFERRED EMBODIMENTS

In this detailed description of the present inventive fluorescence instrument certain terms are synonymous in meaning and interchangeably used. The term waveplate and retarder are both used to denote an optical retarder element having a selected optical retardance. Wavelength band and wavelength range are both used to denote a contiguous range of wavelengths, which typically spans a few nanometers or more, but may be monochromatic in some cases such as when discussing laser light or spectral line emission from lamps. Fluorescence instrument, instrument, fluorescence reader, and plate reader all refer to an instrument for quantifying the amount, polarization, or time-evolution of fluorescent light from a sample.

Figure 1:
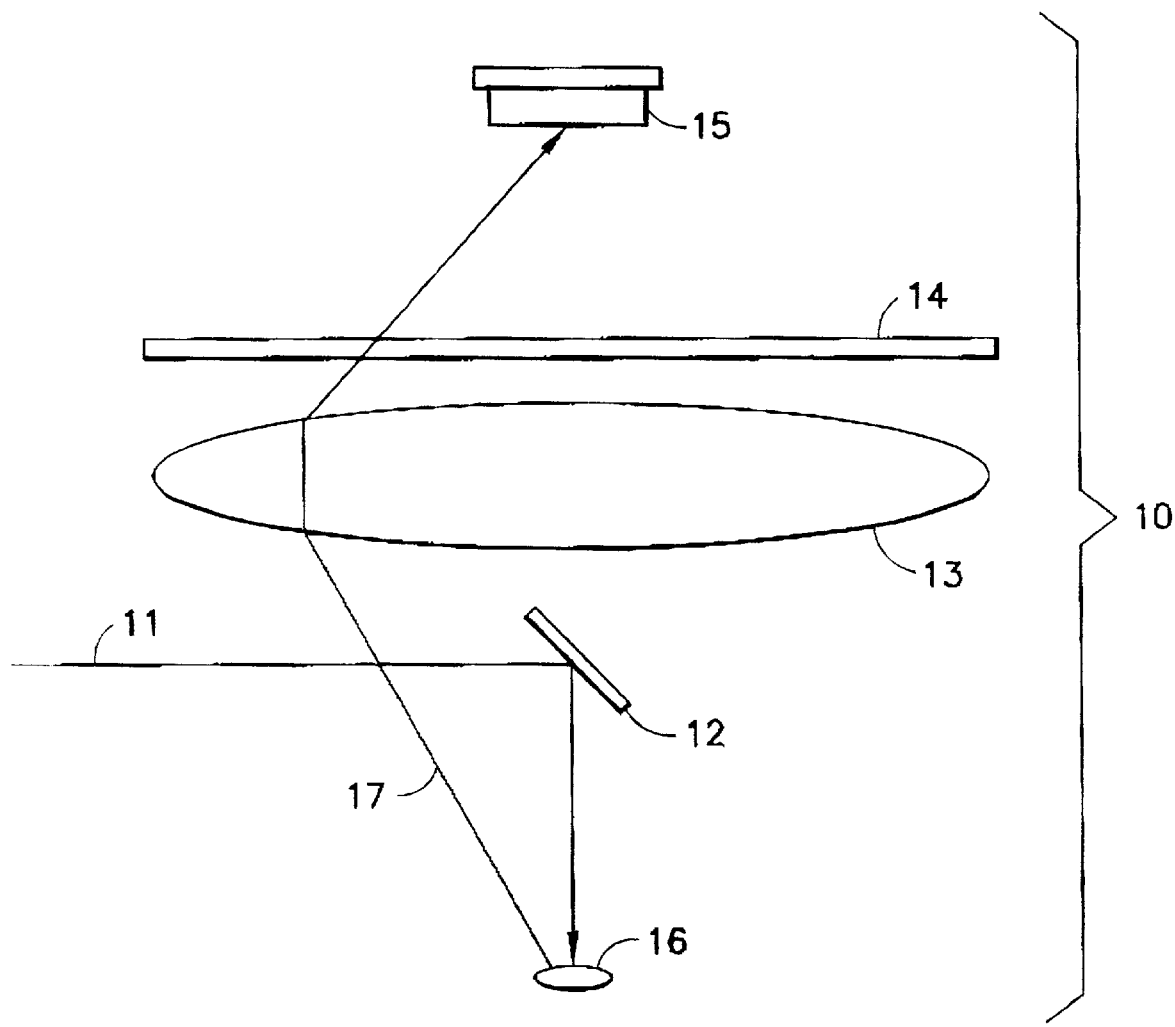
FIG. 1 shows a side-view of the illumination and collection optics for a fluorescence instrument according to the present invention.

FIG. 1 depicts a fluorescence reader 10 in accordance with the present invention. Light rays 11 reflect from a mirror 12 and are directed onto a sample 16. Ideally, the light rays form a relatively compact bundle, so the mirror is small and blocks a negligible portion of the aperture of lens 13. Rays 17 of fluorescent emission are imaged by a primary objective 13 to form an image of the source at detector 15. A barrier filter 14 rejects light having the wavelength of the excitation light, and transmits light having selected wavelengths that are characteristic of the emission light.

A number of aspects of this arrangement bear discussion. First, the arrangement is well suited for multi-spectral imaging. To perform fluorescence excitation or emission spectroscopy, only the wavelength of excitation light 11 and the barrier filter 14 need to be varied. These are readily achieved by means of filter wheels, gratings, or tunable filters such as liquid crystal tunable filter (LCTF) or acousto-optic tunable filter (AOTF) devices. These components provide high speed tuning (50 ms or less). Examples of fluorescent probes for which the emission wavelength is not widely separated from the excitation wavelength include Bodipy and Alexa probes (both available from Molecular Probes, Inc., Eugene, Oreg.).

Second, there is no dichroic epi-illumination member, such as are commonly used in fluorescence microscopes. The mirror 12 is normally chosen to be reflective at a wide range of wavelengths including the visible and near-UV range. So, there is no need to interchange this element in order to adjust the excitation or emission wavelengths. This eliminates a major barrier to multi-spectral imaging that is present in many fluorescence instruments.

A third benefit is that the excitation light does not pass through objective 13. This eliminates the possibility of fluorescence being generated within the objective, or of excitation light being scattered from lens surfaces back toward the detector. The instrumental sensitivity is therefore improved, relative to fluorescence instruments where excitation light passes through the objective on its way to the sample.

Another advantage is that by eliminating the dichroic an improved measurement of fluorescence and of fluorescence polarization is obtained. It is well-known that a dichroic element used at non-normal incidence has a different spectral response for light polarized in the plane of incidence (p-polarized) than for light polarized orthogonal to the plane of incidence (s-polarized). As the dichroic is not perfectly transmissive for both states (S- and P-), there is some loss of emission light by reflection at the dichroic, which reduces the total signal. And, the differential spectral response between the S- and P- states means that the amount of reflective loss varies with the state of polarization. Simply put, the dichroic partially polarizes the emission light, which distorts the reading of fluorescence polarization. These effects are most pronounced when using samples for which the emission wavelengths are not widely separated from the excitation wavelengths, as this places the greatest requirements on the dichroic element.

Fourth, the objective only needs to operate at the emission wavelengths. Compared to an epi-illumination objective which must also operate well at the excitation wavelengths, which are often located in the ultraviolet region, this objective sees a more restricted wavelength range and the lens design is simplified as a result.

Figure 2:
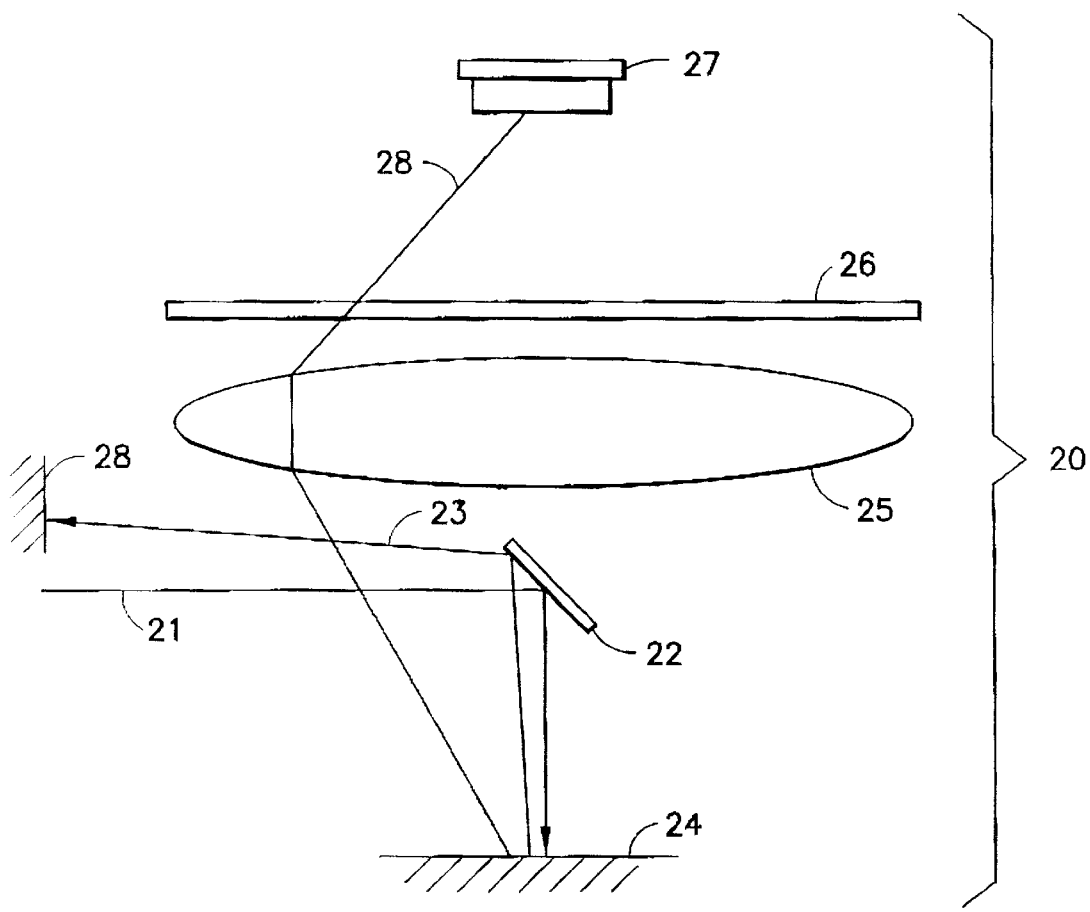
FIG. 2 shows how the optics and sample may be arranged to reject specular reflections and thus improve the detection limit in the fluorescence measurement.

Another benefit of this arrangement is illustrated in FIG. 2. This shows excitation light 21 reflecting from mirror 22 and passing to sample 24 which has a relatively flat specular surface. Rays of excitation light 23 reflected from the sample 24 pass back to mirror 22 and are reflected to a surface 28 which is out of the field of view of objective 25. This traps the reflected light and prevents it from contributing to the image formed at detector 27, further reducing the amount of unwanted excitation light at that component, and improving sensitivity. This method can be used effectively with samples which are prepared in the form of slides, multi-well plates illuminated from below, gel plates, and other sample formats having relatively flat specular surfaces.

Excitation light 11 may be supplied by laser, a laser diode, an LED, or a lamp with a compact arc. If a lamp is used, a bandpass filter is used to select an excitation wavelength range. If a laser or LED source is used, a filter may not be necessary, but a filter or tuning means may be employed if the source is capable of multi-wavelength operation.

When constructing instruments for use with multi-well plates, the source is preferably a laser and the beam is not focused to a point at or within the sample. Rather, in passing through the sample, the beam defines a right cylinder with a height as set by the sample thickness and a diameter set by that of the beam. It is normally best not to illuminate the sample well walls, since the optical properties at the walls often are not representative of the bulk sample material. Not illuminating the walls reduces or eliminates fluorescence components arising from the plate material itself, from nonspecific binding, or from other unwanted sources. This result is readily achieved by choosing a suitable laser beam diameter and insuring that it is placed to avoid illuminating the walls.

In many cases, no further optics are needed to realize this goal. However, it may be desirable to incorporate a lens to produce a converging beam, rather than a nominally collimated beam, with a smaller beam diameter at the sample. It may also be desirable to use spatial mode filters, collimators, optical fibers, coupling optics, and all other optical means, either separately or together, to produce an improved beam profile or to couple various sources into the fluorescence instrument, as is well known in the art. The need for these is dictated by the sample type, source properties, and the like, according to the requirements of the particular instrument being built.

Figure 3:
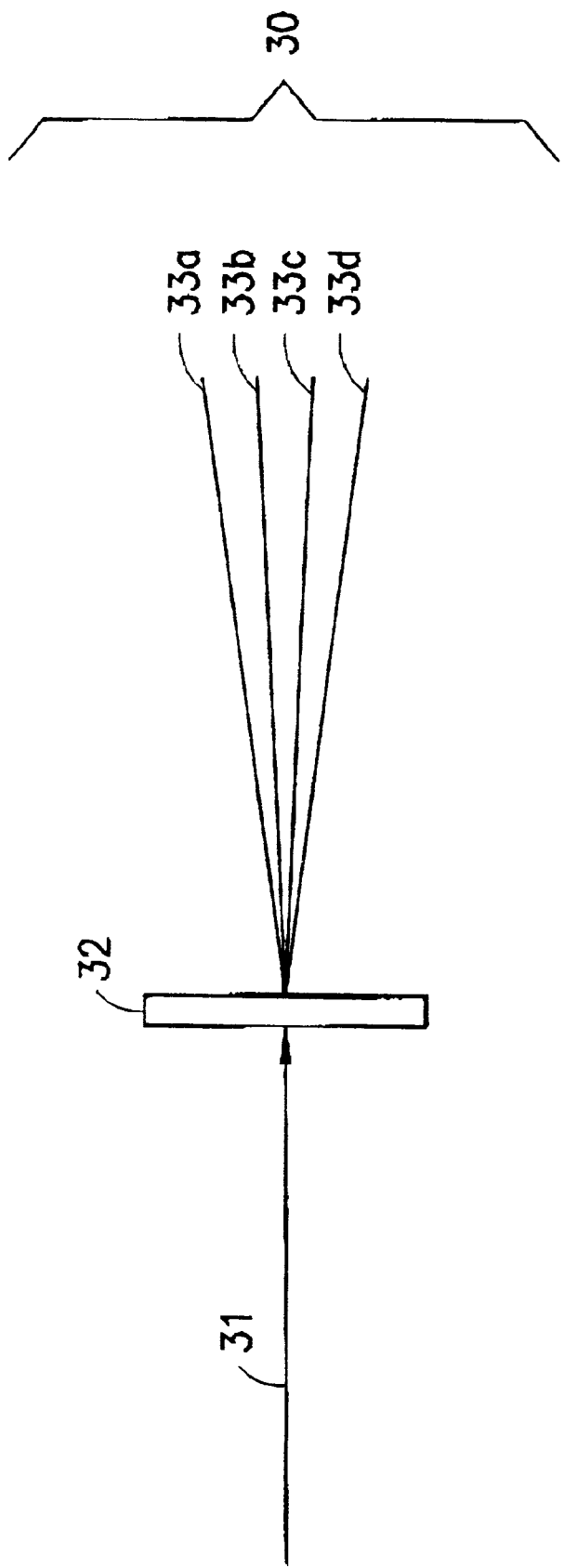
FIG. 3 shows use of a diffractive optical element to produce a selected number of beams with approximately equal intensity, separated in angle of propagation, from a single input beam.

The present invention can easily read a large number of samples at once. FIG. 3 illustrates a multiple-beam source 30 consisting of an incident beam 31, a beam-dividing diffractive optical element 32, and multiple output beams 33a, 33b, 33c, and 33d. The diffractive element 32 produces a selected number of distinct beams according to its diffractive properties, and commercially available devices are available from MEMS Optical Inc. (Huntsville, Ala.) including the model 1011-488 for producing 16 output beams in a fan pattern, with a separation of approximately 2 degrees between the endmost beams. The output beams are of high optical quality and have approximately equal energy in each beam. In this way, distinct illumination spots of approximately equal power are available for exciting a plurality of samples, using a single illumination source.

Figure 4A:
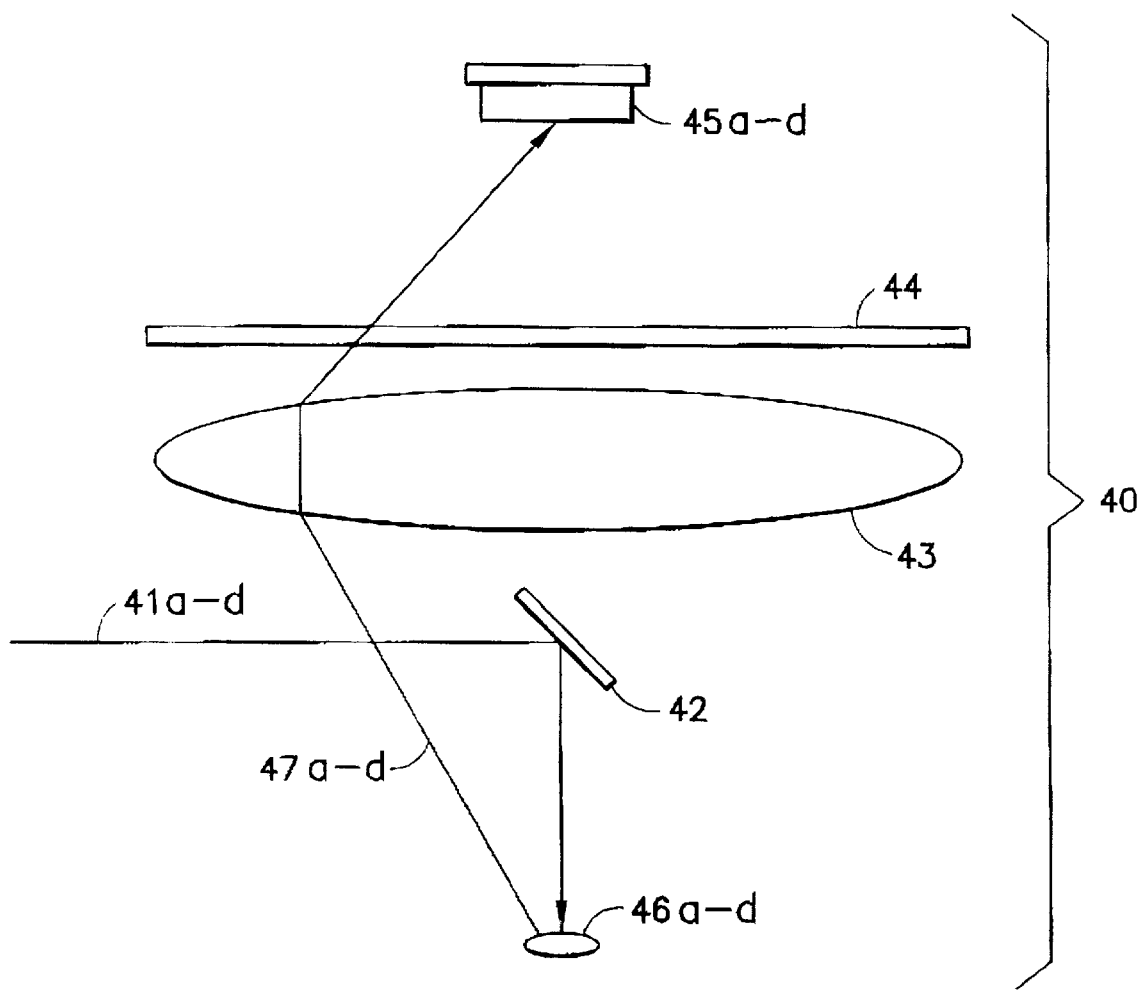
FIG. 4a shows in side-view a fluorescence instrument capable of reading simultaneously several samples arranged in a line, as viewed from along the axis defined by the samples.

FIG. 4a shows a side-view of an instrument that incorporates a multiple-beam source. In this view, the various beams are separated in the dimension extending into and out of the plane of the drawing, and excite a plurality of samples. The design is identical to that shown in FIG. 1, except that multiple beams, samples, and detector elements are used. The transverse side-view view 4b of the same instrument illustrates more clearly the relationship between the beams, samples, and detector regions. Distinct beams 41a–d reflect from mirror 42 and excite samples 46a–46d. The samples are arrayed in a line, with an inter-sample spacing equal to the separation between beams. Mirror 42 has sufficient length to span the array of samples, but it is small in the orthogonal dimension, so its area is minimized and it does not greatly occlude objective 43. Fluorescent emission 47a–d from these samples is collected by objective 43 and forms images at detector elements 45a–d. Filter 44 rejects stray or scattered excitation light and defines the wavelength band for the emission signal.

The instrument 40 has significantly higher throughput than a single-sample fluorescence instrument, since it simultaneously reads many samples. This performance increase is achieved with little added complexity or cost: mirror 42 is extended in one dimension, a diffractive optical element is added to create multiple beams, and a pixelated detector is used to provide independent detector elements. Optical performance is not degraded relative to a single-sample system, although the lens must adequately image multiple samples rather than a single sample. This requirement is not difficult to meet using designs in the existing optical art. Multiple objectives are not required. While the excitation beam is divided among N samples, resulting in lower flux density and lower fluorescence signals, many lamp and laser sources provide sufficient flux that lowered excitation flux is not a practical concern; indeed, it is often necessary to include neutral-density filters in existing systems to avoid sample overexposure and premature photobleaching.

The arrangement of excitation and emission optical paths in the present invention yields an important benefit in polarization-sensitive measurements. Beams of excitation light 41a through 41d (after reflection by mirror 42) are nearly parallel to the optical axis of the objective 43. If they derive from plural light sources, the direction of propagation for each beam may be adjusted separately; if they derive from a single light source and a beam division element, the beams appear to fan out from the virtual image of the division element as reflected by mirror 42. In either case, the multiple beams can be made to have propagation vectors which lie within a few degrees of the optical axis of objective 43. This near-coincidence of optical axes for excitation and collection in the present invention is termed coaxial illumination.

Figure 5:
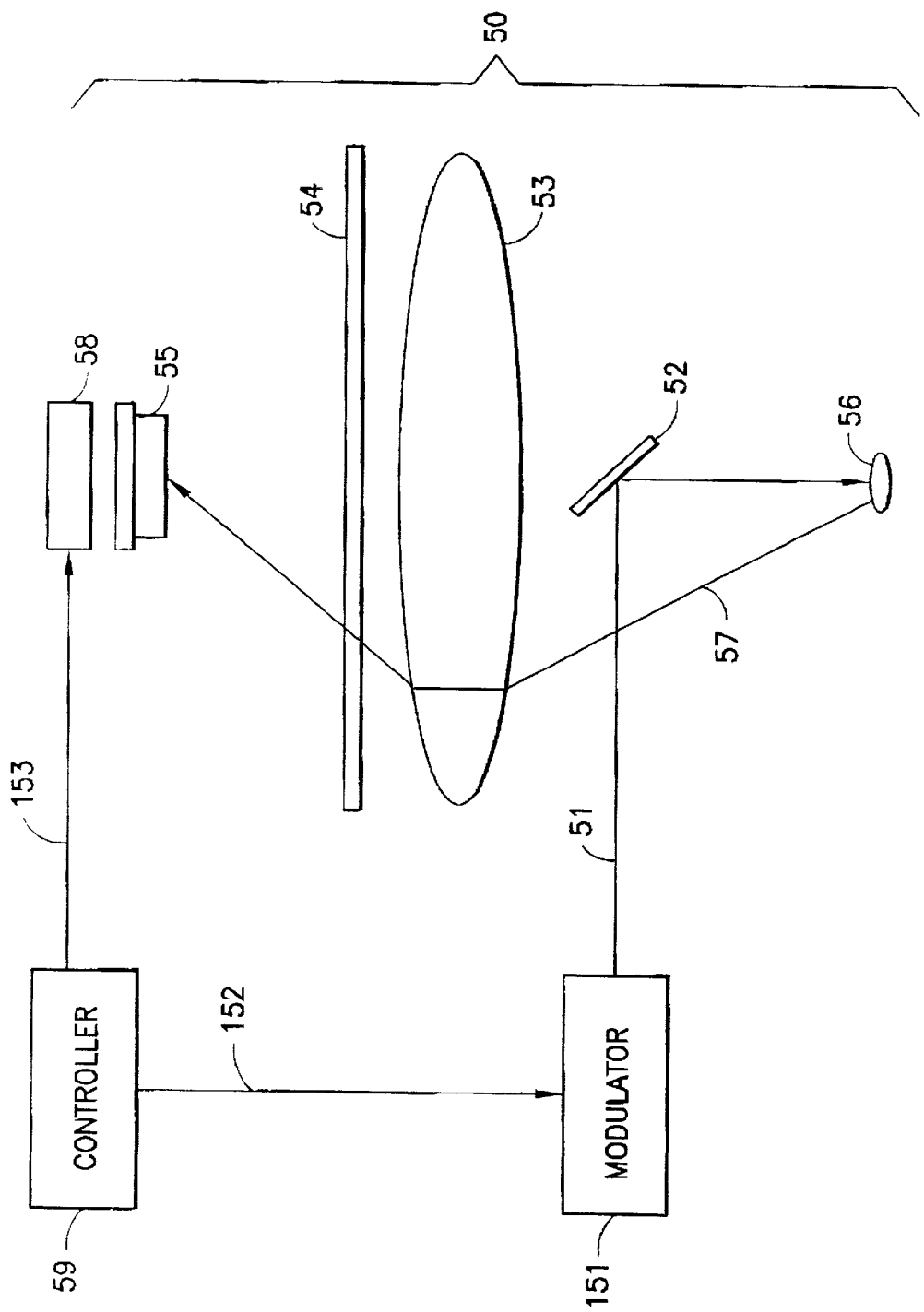
FIG. 5 shows in side-view a fluorescence instrument for performing measurements of time-resolved fluorescence of several samples, incorporating a modulated beam for excitation and a detector with a photosensitivity that is time-gated according to control means.

If the propagation of beams 41a–41d are parallel to the optical axis of objective 43, and objective 43 is telecentric in the optical path region containing samples 46a–46d and in the image plane, then the axis of polarization of excitation light will not be distorted by the imaging system. That is, orthogonal polarization states in the excitation beams 41a–41d will appear orthogonal in the image plane at detectors 45a–45d. Similarly, rotating the plane of polarization by an angle dθ in any of the beams 41a–41d will result in a rotation by the same angle dθ at the detectors 45a–45d. This property enables quantitative measurement of polarization states. Substantially the same result is obtained if excitation beams 41a–41c lie within a few degrees of the optical axis of objective 43. The apparatus of this invention may be used for time-resolved fluorescence, as illustrated in FIG. 5. Fluorescence instrument 50 incorporates a beam 51 having an intensity that is modulated by element 151 in response to control signal 152 from controller 59. Detector 55 incorporates adjustment means 58 for altering its photosensitivity in response to control input 153 from controller 159. These enable time-resolved measurements of fluorescence, to resolve species with different excitation lifetimes. Objective 53 collects the emission light rays 57 from sample 56 and filter 54 transmits light in a selected wavelength range to the detector 55.

Figure 6:
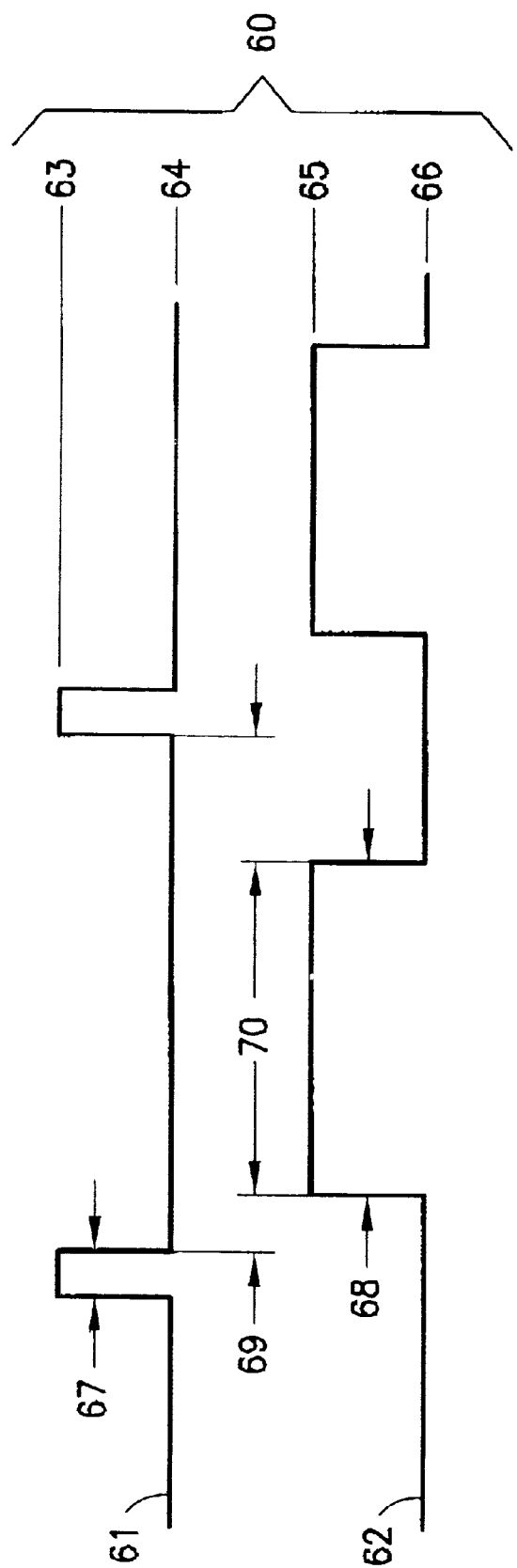
FIG. 6 illustrates schematically the timing relationship between modulation of the excitation source and time-gating of the detector photosensitivity.

A simple type of time-resolved fluorescence is diagrammed in FIG. 6. Timing diagram element 61 indicates the flux level in beam 51, as it is varied between a high flux level 63 and a low flux level 64. Bursts of excitation light have a time-duration indicated by 67. In concert with this, the detector photosensitivity 62 is varied between a highly responsive state 65 and a non-responsive state 66. The detector is non-responsive to light during the period of high excitation flux. After a delay indicated by 69, it becomes photosensitive for a time-duration indicated by 68, then becomes non-responsive again. After a delay indicated by 70, the cycle is repeated.

This discriminates between two populations of molecules, one of which has a relatively long fluorescence lifetime and one of which has a short fluorescence lifetime. The latter, after being excited, quickly decay during the interval indicated as 69. When the detector becomes highly responsive, this species is no longer emitting. Thus the detector records only the species with a long fluorescence lifetime during the interval 68. Such a scheme is often used to selectively view fluorescent markers which have been chemically designed to have a long fluorescence lifetime, while selectively ignoring background fluorescence with a short fluorescence lifetime.

More complex versions of time-resolved fluorescence may be practiced using the arrangement of FIG. 5, such as phase-sensitive detection and quadrature detection. These may be performed at various frequencies to effect a dispersion measurement. The present invention provides a means to perform time-resolved measurements on many samples at once, by incorporating multiple beams and multiple detectors as described above. The excitation beam may be modulated prior to its passage through the diffractive element, so only a single modulator is required.

If a laser or laser diode is used, pulsed or Q-switched operation can be employed to provide a high depth of modulation at little or no additional component cost. Or, a modulator such as a Pockels cells or integrated optical modulator can be used with a continuous (CW) laser. Any of the techniques known in the laser art for intensity modulation may be employed, and depending on the desired goal, one may wish to implement an on-off modulation, or modulation that produces a prescribed intensity pattern such as sine-wave modulation. For lamps, pulsed operation is usually preferred because higher peak flux levels are achieved, but modulation producing a sine-wave or another prescribed pattern could also be employed.

The detector responsivity can be altered by a microchannel plate or intensifier tube, which are well-known in the art as providing means for gating a detector's photosensitivity in a few nanoseconds. Alternatively, a detector may be used which has integral electronic shuttering means to render it non-responsive when this is desired. Certain types of charge-coupled device (CCD) detectors provide this feature. Any technique which alters the photosensitivity of a detector would be suitable, so long as it provides the desired modulation.

Figure 7:
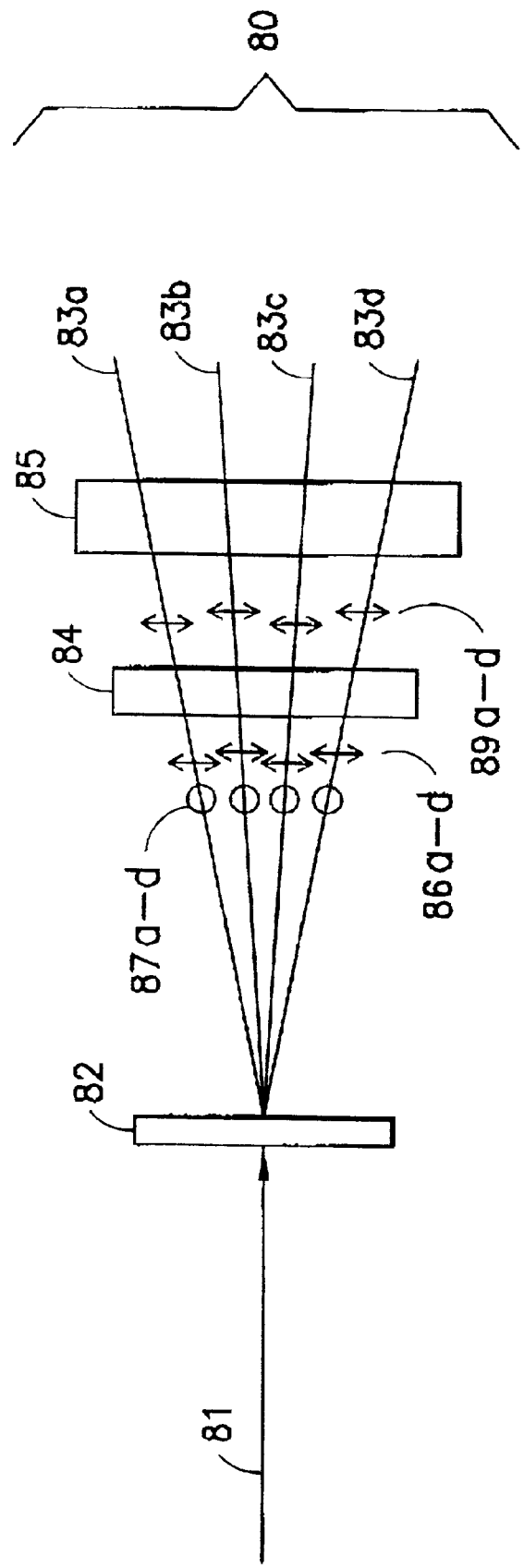
FIG. 7 shows the use of a polarizer and polarization modulator in optical series with a diffractive optical element, to produce a selected number of beams with approximately equal intensity, with a polarization state that is well-defined, which may be adjusted for all beams together.

FIG. 7 illustrates a system 80 for controlled modulation of the polarization state of one or more beams. A linear polarizer 84 transmits only those components 89a–89d having a specified polarization state, to a polarization modulator 85 which imparts a selected polarization rotation or retardation to all beams 83a–83d. This arrangement eliminates any polarization effects which may be introduced to the incident beam 81 by diffractive beamsplitter 82, that might cause the polarization state to differ from one beam to another. Suitable linear polarizer elements include a sheet dichroic polarizer such as HN-38S from Polaroid Corp. (Norwood, Mass.), or a Glan-Taylor polarizer from Karl Lambrecht (Chicago, Ill.). Polarization rotator elements include passive optical components such as waveplates, or active electro-optical components such as liquid crystal cells. Suitable waveplates include NRZ type film from Nitto Denko (San Jose, Calif.). A waveplate may be mechanically engaged and disengaged from the beam to effect switching, or the waveplate may be rotated. It is well-known that when a half-wave plate is placed in a linearly polarized beam with its slow axis at an angle φ to the polarization axis of the beam, the polarization axis of the beam is altered by 2φ in passing through the half-wave plate. Liquid crystal cells include variable retarder cells from Meadowlark Optics, preferably with the slow axis of the liquid crystal cell oriented at 45 degrees to the polarization axis of linear polarizer 84. Such a cell transforms linearly polarized light beams 89a–d to the orthogonal polarization state, or to left- or right-circular polarization, when it exhibits retardance values of $\lambda/2$, $\lambda/4$, and $3\lambda/4$. The beam is unaltered at a cell retardance value of 0 or $\lambda$.

Figure 8:
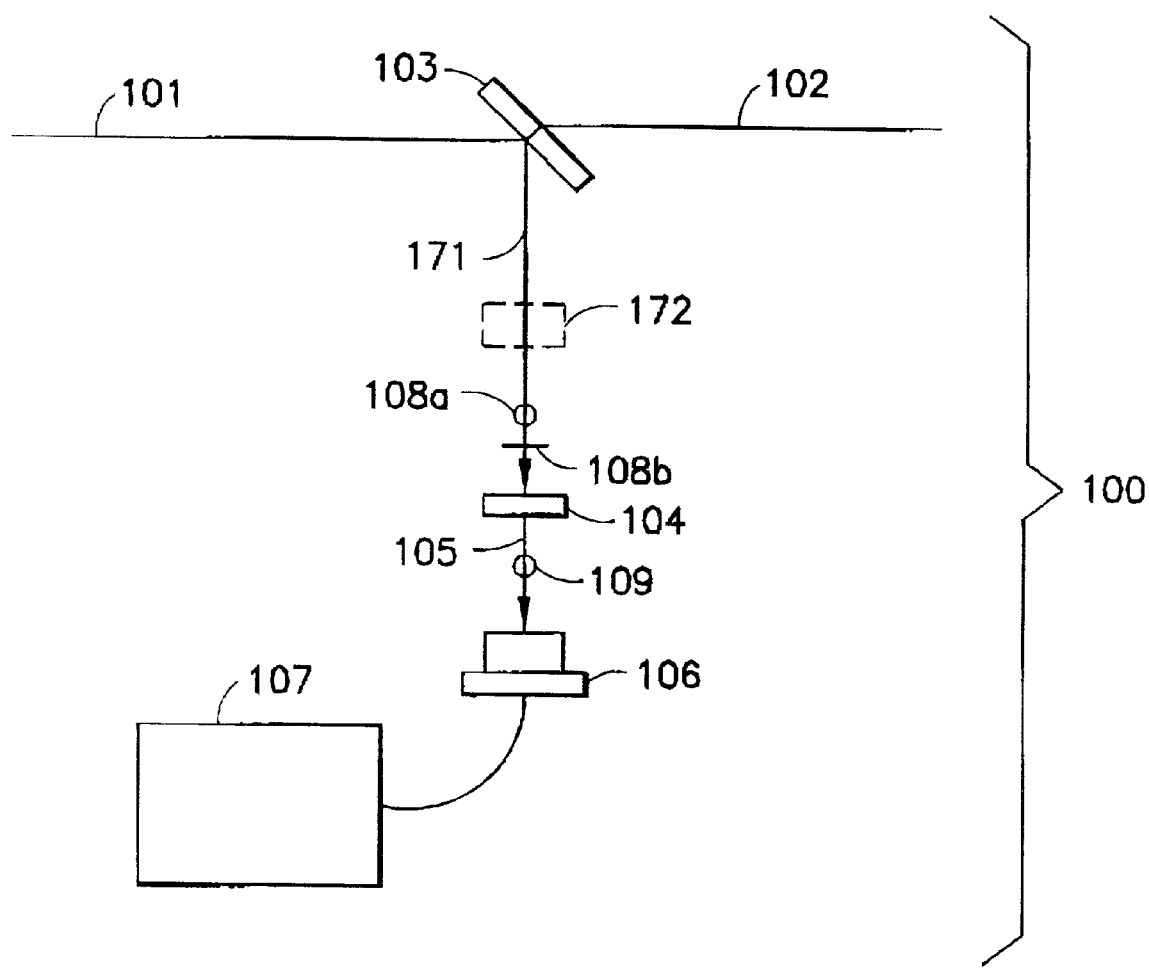
FIG. 8 shows a means for monitoring the polarization state of one of the polarization-modulated beams.

The polarization state of one or more beams may be monitored using the polarization measuring arrangement 100 of FIG. 8. Incident light 101 reflects from reflector 103 to produce a beam 171. This beam has polarization components 108a and 108b, which are conventionally referred to as the S and P states of polarization. Polarization analyzer 104 transmits a single polarization state of light 109 in beam 105 to a photodetector 106 which is connected to readout electronics 107.

While FIG. 8 indicates that polarization state 109 is the linearly polarized S state, it could be the P state or any other linear polarization state; it could also be any circular or elliptically polarized state. Polarization analyzers 104 for transmitting circular or elliptical states can be constructed using methods of the prior art, such as by combining a linear polarizer with an optical waveplate. The polarizer and waveplate types listed above are suitable for this purpose. Suitable photodetectors include photodiodes, photomultiplier tubes, or CCD detectors. These components are all available from Hamamatsu Corporation (Middlesex, N.J.).

Reflector 103 may be a partial reflector such as a beamsplitter or an uncoated glass window, or it may be the high-reflectivity mirror used to direct excitation light to the sample. In the case of a partial reflector, beam 102 contains significant flux and fluorescence measurements may be made while the polarization measurement system 100 is operating. In the case of a highly reflective mirror, there is little or no flux in beam 102. Instead, the polarization measurement system 100 operates in alternation with actual measurements of fluorescence from samples. Components 104 and 106 are located in the optical path normally used for the sample, and directly view the excitation beam. Polarization measurement system 100 may be mechanically engaged or disengaged from the beam, or it may be permanently located in the beam at a location downstream from the position 172 where the sample is placed.

The system 100 is often useful in connection with the controlled polarization modulation system 80 of FIG. 7. Modulation system 80 may be used to adjust the polarization state while the result of each adjustment is measured with polarization measuring system 100. Polarization measuring system 100 acts as a sensor that provides feedback to the polarization adjustment process.

Other aspects of the system 100 become important when controlled adjustment of polarization state is sought. Typically, the intensity of laser or lamp sources is not perfectly controlled. Variations in lamp intensity render it difficult to maximize a given polarization state by seeking a maximum in the signal from photodetector 106. Rather, it is preferable to select polarization analyzer 104 to transmit the polarization component 109 which is orthogonal to the desired polarization state. By seeking a minimum in the orthogonal signal 109, the desired component is maximized. Since a value of zero is sought, modest fluctuations in the incident beam 101 do not hinder the adjustment process.

If multiple beams are used in the fluorescence system, it is preferable that the beams have essentially the same polarization state. Then, by monitoring the reading of photodetector 106 in any given beam, the polarization component 109 is determined for all beams at once.

In a multiple-beam arrangement, beamsplitter 103 may sample more than one beam and direct the plural sample beams through plural polarization analyzers to plural detectors, each of which is connected to readout electronics. The polarization analyzer 104 need not be the same in each beam. Rather, the various polarization analyzers 104 may be constructed to select various polarization states 109. By seeking a minimum (maximum) intensity in a given photodetector 106, the content of the associated polarization state 109 is minimized (maximized) for all beams. This process may be repeated for the signals from various photodetectors 106, to produce a sequence of polarization states that contain a minimum (maximum) content of various polarization states 109.

Figure 9:
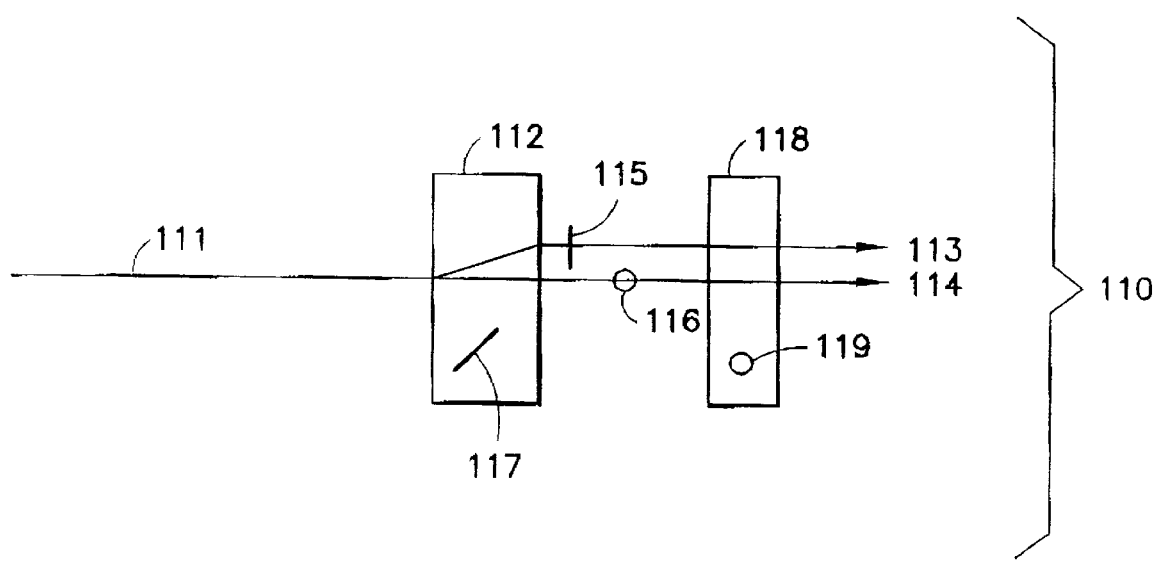
FIG. 9 shows the use of a double-refractive calcite slab to spatially separate the polarization components of a beam onto distinct photosensitive regions of a detector.

FIG. 9 illustrates a polarization beam separator 110 which is especially well-suited to the present invention. Light beam 111 encounters double-refractive element 112 having an extraordinary axis 117 which is inclined at a non-zero acute angle to the beam. In passing through element 112, beam 111 is separated into beams 113 and 114. Beam 114 contains polarization component 116 and passes through element 112 without substantial deviation, while beam 113 contains linear polarization component 115 which is orthogonal to component 116 and is spatially deflected. The propagation of light through double-refractive crystal elements is described in standard optics texts such as Max Born and Emil Wolf, "*Principles of Optics*" (Pergamon Press, New York, corrected 6th Edition, 1980 and 1993).

The thickness, composition, and extraordinary axis orientation of element 112 are selected to completely separate beams 113 and 114. Typically, element 112 is constructed of calcite because of its high value of $n_e/n_o$, but quartz, lithium niobate, ammonium dihydrogen phosphate (ADP), potassium dihydrogen phosphate (KDP), oriented liquid crystal polymers, or any other double-refractive material may be used. Calcite elements may be obtained from Karl Lambrecht (Chicago, Ill.).

Because the optical path length in the double-refractive element is different for beams 113 and 114, these beams will form images at different focal planes if polarization separator 110 is placed in a convergent imaging system. This path length difference can be compensated by a second double-refractive element 118 with an extraordinary axis 119 that is substantially normal to the propagation axis of beams 113 and 114. This second element 118 does not significantly displace either beam, but introduces a compensating path length so beams 113 and 114 will come to a focus at the same plane. The composition, material, and orientation used in element 118 can be readily calculated according to the prior art for birefringent optics, to achieve the function of compensating the optical path difference introduced by element 112.

Figure 10A:
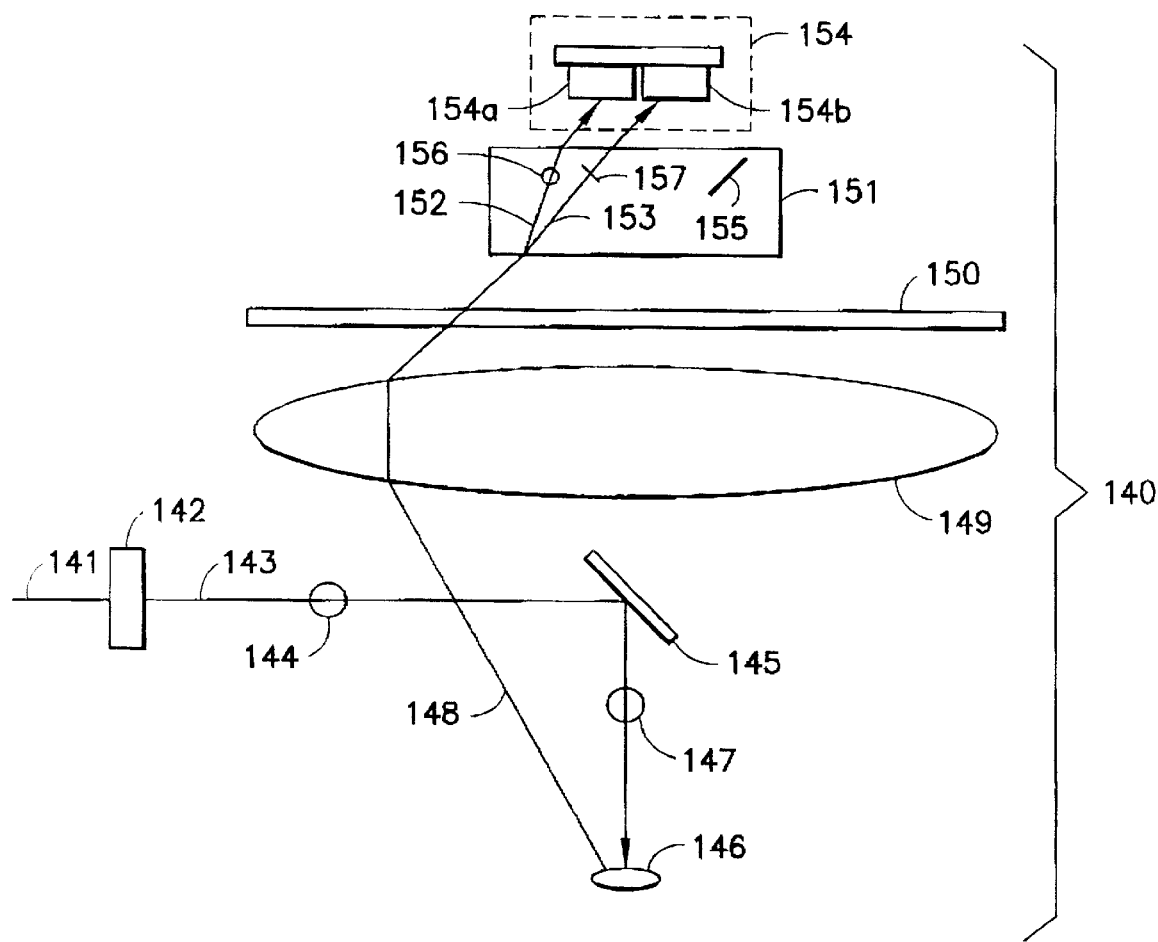
FIG. 10a shows a fluorescence instrument taking a first measurement as part of an assay of fluorescence polarization.

A complete system 140 for fluorescence polarization (FP) measurement is pictured in FIG. 10a. Excitation light beam 141 passes through a system for controlled modulation of polarization 142, emerges as beam 143 with linear polarization state 144, reflects at mirror 145 with polarization state 147 and excites sample 146. Fluorescent emission light ray 148 is collected by objective 149 and passes through a filter 150 which selectively transmits fluorescent light in a selected wavelength band and rejects stray or scattered excitation light. Light ray 148 encounters double-refractive element 151 and is spatially separated into components 152 and 153 with linear polarization states 156 and 157, respectively, which are sensed at photodetector elements 154a and 154b oil photodetector array 154. The signal from detector 154a indicates the intensity of light having the same polarization state as the excitation beam, while the signal from detector 154b indicates the intensity of light which has the orthogonal polarization.

From the measurement depicted in FIG. 10a, a rough measure of the fluorescence polarization (FP) may be had. If the signal levels at detector elements 154a and 154b are termed A and B, respectively, the degree of polarization (DOP) may be calculated as:

$$DOP=1000*(A-B)/(A+B) \qquad [2]$$

The limitations of this approach are follows. It is relatively straightforward, using the present invention, to produce light having a high degree of polarization purity 147 at the sample. It is within the existing optical art to produce an objective 149 for the current invention which substantially preserves linear polarization components in fluorescent light ray 148 without conversion into circular or elliptical polarization states. So, the optical system 140 excites the sample with a single, pure linear polarization state and properly resolves the fluorescent emission into its orthogonal components.

However, objective 149, filter 150, and double-refractive element 151 typically exhibit different transmissions when passing light in polarization state 156 versus state 157. And, the response of photodetector elements 154a and 154b are not identical. So, the readings A and B do not accurately indicate the relative proportion of each polarization component in the sample emission light. If the responsivity of photodetector elements 154a and 154b differs by 1%, the measurement of FP will be in error by 10 milli-polarization units (MPU). Similarly, differential transmission of the two polarization states of 1% would produce the same error of 10 MPU. Many applications require accuracy of 1–2 MPU, which exceeds the capability of present-day detectors and optics when FP is determined by a single measurement of the type shown in FIG. 10a.

Figure 10B:
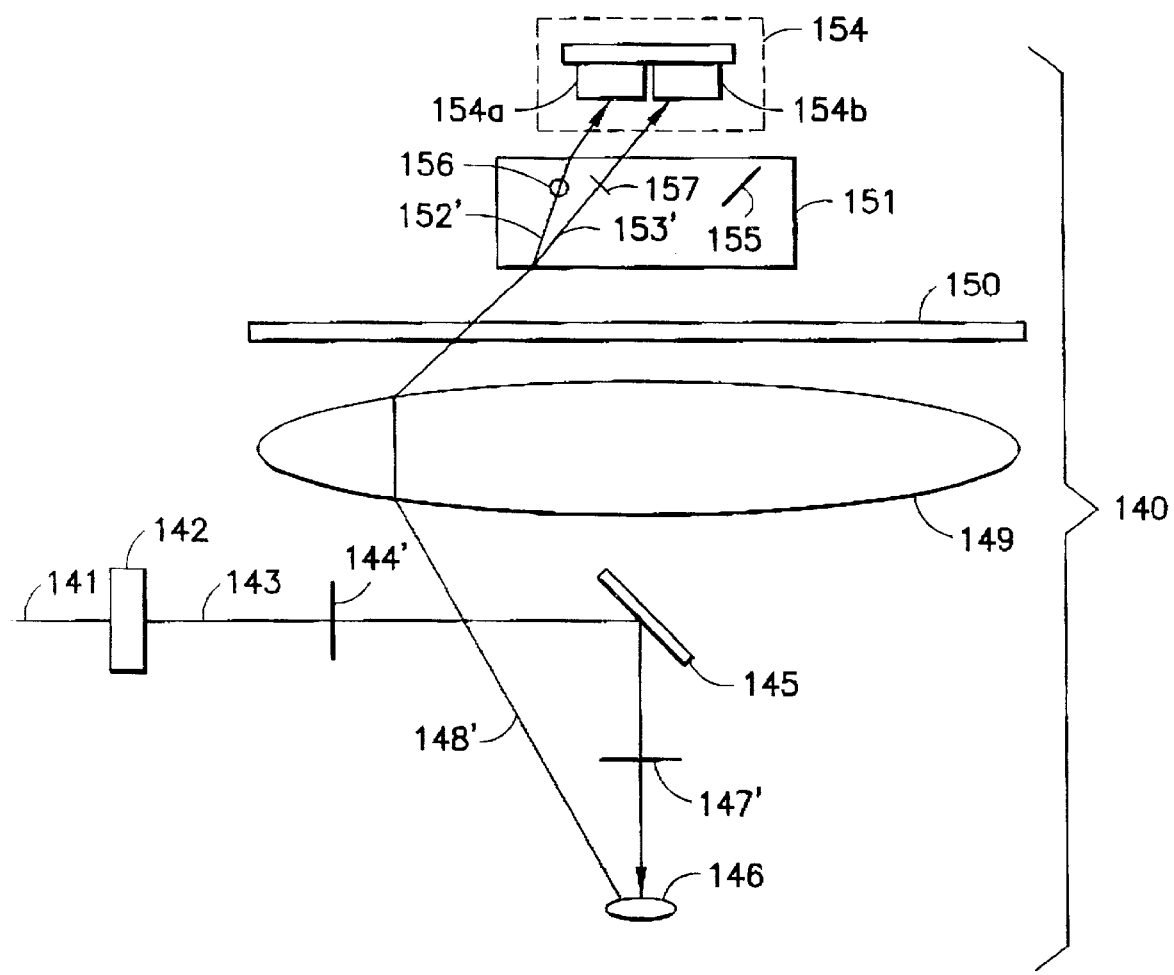
FIG. 10b shows a fluorescence instrument taking a second measurement as part of an assay of fluorescence polarization.

An improved determination of FP is obtained when the measurement of 10a is combined with a second measurement indicated in FIG. 10b, which differs from 10a in that excitation light 143 exhibits polarization states 144' and 147' which are orthogonal to the states 144 and 147. Fluorescent emission 148' is characteristic of the sample 146 under illumination by the orthogonal polarization state. It is similarly resolved into distinct beams 152' and 153' which are sensed at photodetector elements 154a and 154b. The signal from detector 154a indicates the intensity of light having the orthogonal polarization state to the excitation beam, while the signal from detector 154b indicates the intensity of light with the same polarization as the excitation beam.

If the intensity readings obtained at elements 154a and 154b under the conditions of FIG. 10b are termed C and D, an improved measure of the fluorescence polarization (FP) is given by:

$$DOP = 1000*[(A - B + D - C)/(A + B + C + D)] \quad [3]$$

The method of taking two measurements under conditions of FIG. 10a and 10b, and reducing the results according to equation [3], yields a perfect determination of FP when the intensity of excitation beam 147 and 147' is equal for the two measurements. This is readily shown. Suppose that the overall collection efficiency of the optical system, incorporating losses in all optical elements and responsivity in the photodetector, is expressed as $\alpha$ for light having polarization state 156, and $\beta$ for light having the orthogonal polarization state 157. Signals A through D are then:

$$A = \alpha I_{156} = \alpha I_\| \quad [4a]$$

$$B = \beta I_{157} = \beta I_\perp \quad [4b]$$

$$C = \alpha I_{156} = \alpha I_\perp \quad [4c]$$

$$D = \beta I_{157} = \beta I_\| \quad [4d]$$

where $I_\|$ and $I_\perp$ refer to the fluorescence emission in the same polarization state as the excitation beam, and the orthogonal state, respectively.

When equation 3 is evaluated, the result is:

$$\begin{aligned}DOP &= 1000*(\alpha I_\| - \beta I_\perp + \beta I_\| - \alpha I_\perp)/(\alpha I_\| + \beta I_\perp + \beta I_\| + \alpha I_\perp) & [5a]\\ &= 1000*[(\alpha + \beta)*(I_\| - I_\perp)]/[(\alpha + \beta)*(I_\| + I_\perp)] & [5b]\\ &= 1000*(I_\| - I_\perp)/(I_\| + I_\perp) & [5c]\end{aligned}$$

exactly as defined by equation 1. There is no need to compensate for, or calibrate, the optics or detectors. Readings of FP obtained this way are inherently self-calibrating.

This felicitous result is only obtained when the excitation beams in polarization states 147 and 147' have equal intensity. This is difficult to achieve in practice, due to fluctuations in the excitation source beam 141, to polarization-dependent losses in the polarization modulator 142, mirror 145, and to polarization-dependent losses in such other components as may be present in various realizations of this invention. These lead to variations between the intensity of excitation flux in the setting shown as 10a and that shown as 10b. Further, the lamp fluctuations are random, so cannot be calibrated out.

A better method for calculating FP from the same measurements A, B, C, and D is the following:

$$DOP = 1000*[A - B + \gamma(D - C)]/[A + B + \gamma(D + C)] \quad [6a]$$

where $$\gamma = [(A*B)/(C*D)^{1/2}] \quad [6b]$$

Equation 6 yields a perfectly accurate measure of FP even when the source intensity varies between the measurement of A and B, and the measurement of C and D. The accuracy is obtained whether the variation is systematic, as may arise from optical elements 142, 145, or others not pictured; or random, as may arise from lamp fluctuations.

Denote the intensity of excitation light during the measurement of A and B as $I_0$, and that during the measurement of C and D as $kI_0$. Then, we may write equations analogous to 4a–4d that incorporate the difference in intensity:

$$A = \alpha I_{156} = \alpha I_\| \quad [7a]$$

$$B = \beta I_{157} = \beta I_\perp \quad [7b]$$

$$C = k\alpha I_{156} = k\alpha I_\perp \quad [7c]$$

$$D = k\beta I_{157} = k\beta I_{81} \quad [7d]$$

The veracity of equation is then apparent by direct substitution. Substituting first into 6b, $$\begin{aligned}\gamma &= [(A*B)/(C*D)]^{1/2} = [(\alpha I_\| * \beta I_\perp)/(k\alpha I_\perp * k\beta I_\|)]^{1/2} & [8a]\\ &= [\alpha\beta I_\| I_\perp / k^2 \alpha\beta I_\| I_\perp]^{1/2} = 1/k & [8b]\end{aligned}$$

and then into 6a, $$\begin{aligned}DOP &= 1000*[A - B + (D - C)/k]/[A + B + (D + C)/k] & [9a]\\ &= 1000*[\alpha I_\| - \beta I_\perp + (k\beta I_\| - k\alpha I_\perp)/k]/ & [9b]\end{aligned}$$

-continued $$[\alpha I_\| + \beta I_\perp + (k\beta I_\| + k\alpha I_\perp)/k]$$

$$= 1000*[(\alpha+\beta)*(I_\| - I_\perp)]/[(\alpha+\beta)*(I_\| + I_\perp)] \quad [9c]$$

$$= (I_\| - I_\perp)/(I_\| + I_\perp)$$

which is in agreement with the definition of DOP given in equation 1.

The present invention thus provides a means and method for performing measurements of fluorescence and fluorescence polarization which are inherently self-calibrating, by using two measurements of the type indicated in FIG. 10a and 10b, and calculating the FP using equations 6a and 6b. The results are not affected by systematic or random variations in the intensity of the excitation beam, nor by differences in the transmission of the optical system for orthogonal polarization states of fluorescent light, nor by different responsivities of the photodetectors 154a and 154b used to detect the polarized components of fluorescent emission.

Figure 4B:
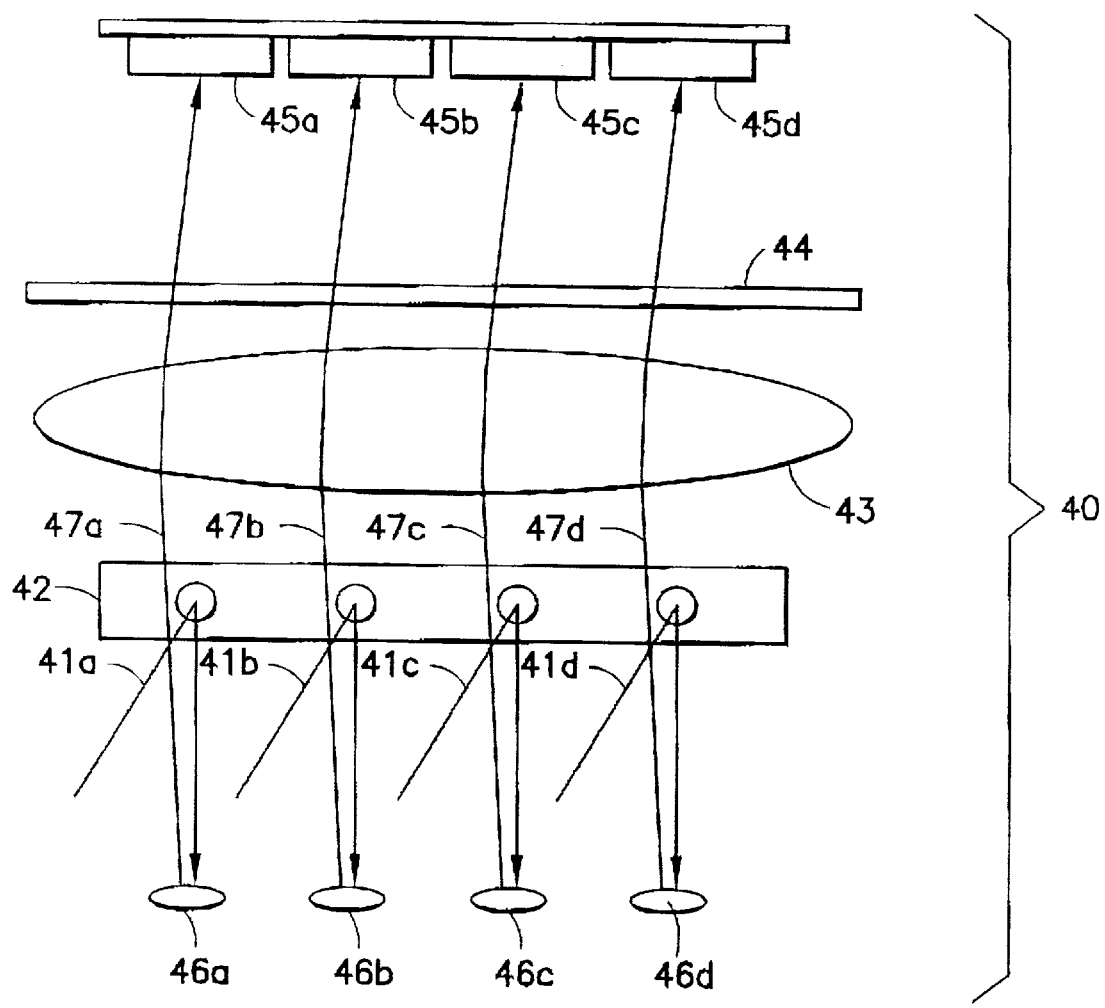
FIG. 4b shows in side-view a fluorescence instrument capable of reading simultaneously several samples arranged in a line, as viewed transversely to the axis defined by the samples.

In practicing the invention, it is important to ensure that the polarization states of excitation light used in the two measurements are indeed orthogonal. In one preferred embodiment, a coaxial illumination system of the type drawn in FIG. 4b is used. An argon-ion laser operating at 488 nm is the light source, with a MEMS beamsplitter to produce 16 beams. A linear polarizer of HN-38S removes any residual polarization that is not polarized with an E-field in the plane of incidence with mirror 145. A liquid crystal variable retarder from Cambridge Research & Instrumentation, Inc. is used as an electrically-selectable zero-wave or half-wave retarder, with its crystal axis at 45 degrees to the polarization vector. The mirror is a first-surface aluminized mirror suspended by fine metal supports at the proper angle, in front of the objective. A 90 mm f/2.5 Tamron (Tokyo, Japan) macro lens is used as the objective, at a 1:1 object:image reproduction ratio. The filter is a longpass interference filter from Chroma Technology (Brattleboro, Vt.), which transmits light with wavelengths above 515 nm. The photodetector is a Princeton Instruments MicroMax cooled CCD camera with a Kodak KAF-1400 sensor chip. A 30 mm plane-parallel slab of calcite with its extraordinary axis at 45 degrees to the surface normal is used as the polarization separator. Objective focus is adjusted to lie halfway between the optimum sample focus for the two polarization states. The calcite slab is oriented to ensure coincidence of the polarization states used for analyzing the fluorescence emission, and the polarization states used for excitation. Proper orientation is achieved when the plane which includes the extraordinary axis and the normal to the slab, also includes the E field of one of the polarization states used for excitation. Orientation may be checked by placing a non-fluorescent, non-depolarizing target at the sample position, illuminating it using one of the polarized excitation states, and observing the signal levels at the two detector spots with the fluorescence wavelength filter removed. When a minimum is attained in one of the spots, the detector is properly oriented.

A polarization measuring system is used, consisting of an HN-38 linear polarizer carefully oriented to select S polarization only, located in front of a laser power meter Model 520 mm from Thorlabs (Newton, N.J.). The drive voltage applied to the liquid crystal was adjusted while the power meter output was noted. The drive voltages corresponding to maximum and minimum power at the meter were noted and used for the measurements of A and B, and C and D, respectively.

One of the benefits of this preferred embodiment is that the detector array consists of pixels in a CCD sensor, which can be reconfigured under software control. The only required hardware change in order to read a new arrangement of samples, is to the beam division optics used to create the multiple excitation beams. Often, only a single MEMS element need be engaged to change sample formats.

Another benefit is obtained when the imaging detector has significantly finer spatial resolution than the minimum amount required to resolve individual spatial regions of the sample. This runs counter to the desire for high signal-to-noise, which favors the use of the minimum number of pixels, thus minimizing read-out noise. However, modem CCD cameras readily achieve the shot-noise limit, at which point photon statistics dominate and noise from the detector and circuitry are secondary. It is useful to consider this in some detail: a typical read-out noise is 8 electrons, and for a back-thinned CCD such as the SPH-5 from Apogee Instruments (Tucson, Ariz.) the quantum efficiency is in excess of 0.8, so the detector noise is equivalent to 10 photons. Provided that the overall signal level exceeds 100 photons per pixel, the measurement will be shot-noise limited.

When determining the fluorescence or fluorescence polarization, the group of pixels corresponding to a given sample region are chosen based on the sample geometry and the illumination pattern. All pixel readings within the region are then summed to derive the total sample flux.

Use of spatial over-sampling, as this is termed, allows for an assessment of measurement quality. In many cases, the sample being measured is essentially homogeneous and the readings of fluorescence should be relatively free of spatial structure except for that imposed by the intensity profile of the excitation beam. The beam profile can be made quite smooth by conventional means such as spatial filtering to the gaussian spatial mode (0,0) as is well known in the optical art. Once this is done, the image of the sample spot, i.e., the distribution of detector intensity readings, should be relatively smooth as well. Presence of dark or light regions within the sample indicate defects in sample preparation such as particulates or bubbles. These can be tested by using image processing techniques such as thresholding against a known profile, and the like. If a sample has an anomalous intensity pattern, i.e., an abnormal distribution, it can be identified as suspect and that information may be used to e.g. require a confirming test of that sample element.

Figure 11:
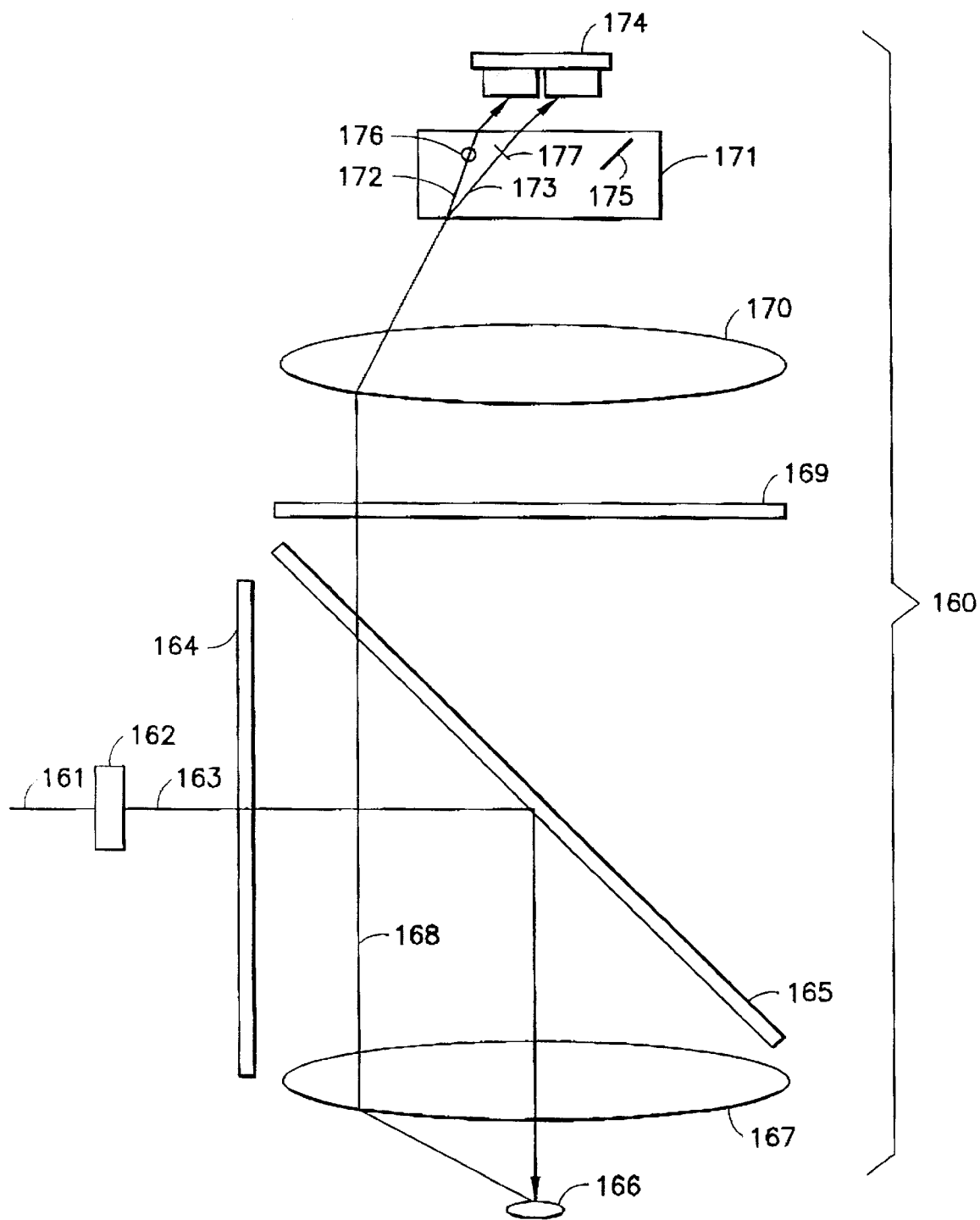
FIG. 11 shows an instrument for measurement of fluorescence polarization according to the present invention, using a prior-art optical arrangement for illumination.

FIG. 11 pictures a system 160 consisting of an epifluorescence microscope of the prior-art type, outfitted with additional components to implement the present invention. Specifically, a polarization modulator 162 is provided to illuminate the sample in sequence with light 163 of two orthogonal polarization states; and, the detector 174 includes a double-refractive polarization separator 171 to produce two distinct images of the sample, according to the polarization state 176 and 177 of the beams 172 and 173 of fluorescence emission light 168. Although elements such as the dichroic epi-illuminator 165 may have significantly different transmission and reflection coefficients for the two polarization components, a perfectly accurate measurement of FP is obtained using equation 6 to analyze the intensities A, B, C, and D at each point in the sample. The orthogonal polarization states are preferably selected as the state whose E-field lies in the plane of incidence of the excitation beam with the epi-illuminator, and the state orthogonal to it. Filters 164 defines the wavelength bands used to excite the sample, and filter 169 defines the wavelength band for emission light passing to the detector 174. Objective 167 and projection lens 170 serve their usual function, and one skilled in the art will appreciate that various implementations are possible in these elements without deviating from the spirit of the present invention. these elements without deviating from the spirit of the present invention.

Figure 12:
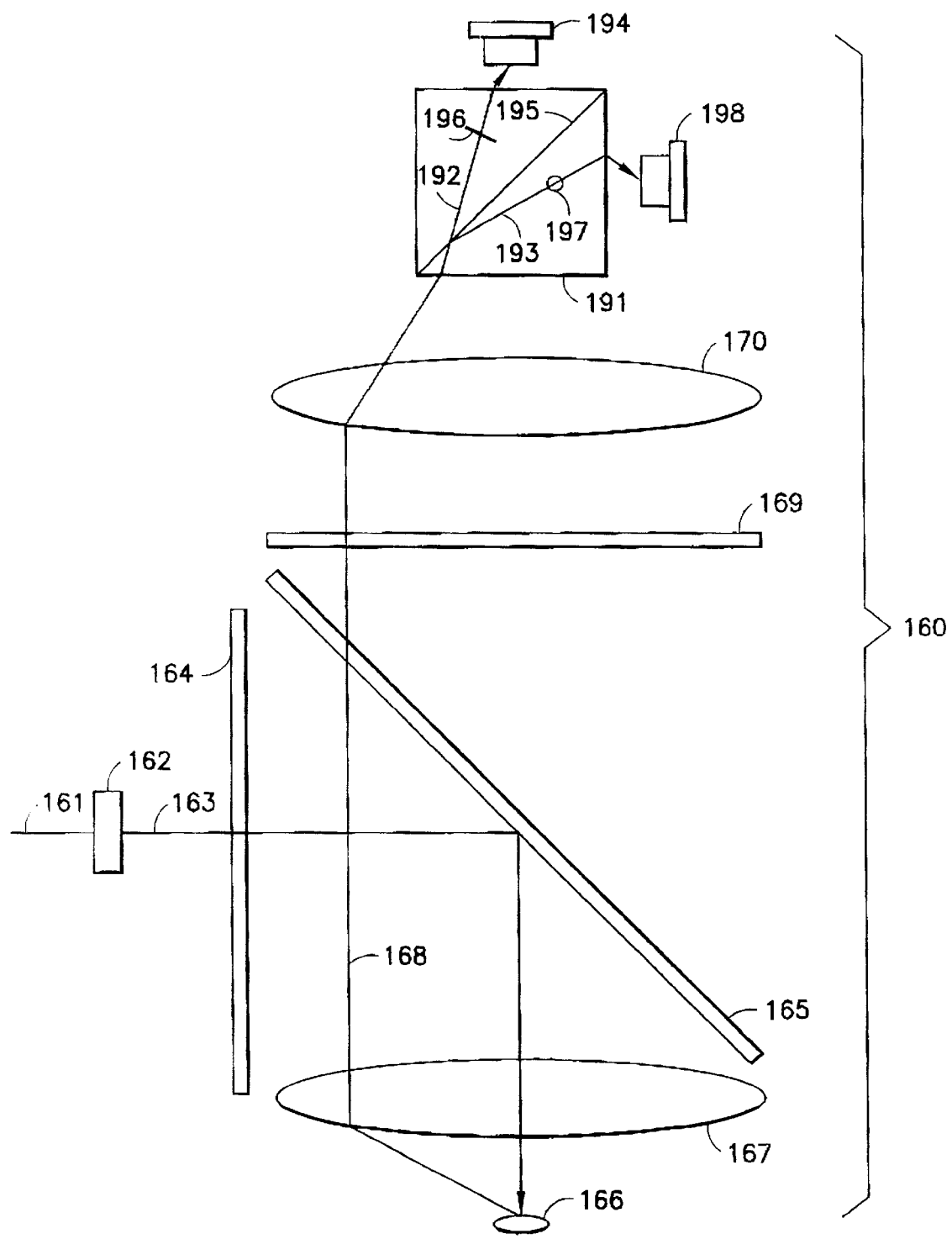
FIG. 12 shows an alternative detector arrangement for measurement of fluorescence polarization according to the present invention, utilizing two detectors and a polarizing beamsplitter cube.

FIG. 12 illustrates an alternative polarization beam separator and detector arrangement. A polarization beamsplitter (PBS) 191 of the conventional right-angle prism type is used to separate the orthogonal components 196 and 197 of fluorescence emission into two rays 192 and 193, and direct them to two distinct detectors 194 and 198. This arrangement is used while the sample is illuminated in light of orthogonal polarization states, to realize the measurements of A and B, and C and D. From these, DOP is calculated using equation 6.

It is explicitly intended that the optical arrangement may be used for a variety of measurements including simple fluorescence, time-resolved fluorescence, multi-band fluorescence, FRET, and all prior-art methods of fluorescence assays. These will enjoy the benefits of the improved optical system in terms of enhanced sensitivity, high throughput, and easy multi-wavelength operation. The techniques taught in this application can be used individually and in combination, such as a time-resolved FRET measurement or other joint modes of use. It is explicitly intended that the teaching of the present invention be used in concert with practices of the prior art, such as compensation for dark-readings, background fluorescence, and the like.

The optical arrangement of the present invention forms the preferred embodiment for FP measurements, by virtue of the coaxial illumination, high sensitivity, and ease of performing measurements on multiple samples at once.

Improved FP measurements are possible in a variety of fluorescence instrumentation, based on the novel two-step measurement and data analysis methods disclosed herein. These measurements have been described in terms of the index of FP cited as DOP in equation 1, but measures of interest other than DOP may readily be calculated from this approach, and data analysis may be performed which is functionally or algebraically equivalent to that described herein without deviating from the teachings and spirit of the present invention. Similarly, approximate measures may be used if full accuracy is not required.

While particular means have been disclosed as preferred embodiments of the functions which support this measurement scheme, such as beam division, polarization measurement, and polarization separation, prior-art means may also be used for these purposes. Finally, while refinements have been taught which are beneficial in many instances, such as the improvement of equation 3 to yield equation 6, or the monitoring of beam polarization by a polarization measurement system, these may be eliminated where no benefit accrues from their use in a given application, or where such benefit is not sought.

Thus, while there have been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same or substantially the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

The invention is not limited by the embodiments described above which are presented as examples only but can be modified in various ways within the scope of protection defined by the appended patent claims.

I claim:

1. A fluorescence measurement instrument comprising
   a plurality of sample regions for receiving samples;
   excitation means that produce a first beam;
   a diffractive optical beamsplitter element that splits the first beam into plural secondary beams, said plural secondary beams simultaneously exciting the plurality of sample regions to effect fluorescence of samples therein; and
   detection means for detecting the fluorescence from the plurality of sample regions.

2. The fluorescence measurement instrument of claim 1, wherein the detection means comprise a detector with plural independent pixel regions for receiving the plural secondary beams.

3. The fluorescence measurement instrument of claim 1, wherein the plurality of sample regions is a multiwell plate having a plurality of wells having well walls separated by inter-sample regions, and
   wherein the plural secondary beams provide substantially no illumination of the well walls or the inter-sample regions.

4. The fluorescence measurement instrument of claim 1 wherein the excitation means comprise a laser source.

5. A fluorescence measurement instrument comprising
   excitation means for providing light;
   a sample region;
   detection means comprising an objective for gathering fluorescence emitted by said sample region and a photodetector for measuring the intensity of the fluorescence gathered by the objective; and
   a mirror located between the sample region and the objective for directing light from the excitation means to the sample region, the mirror being small relative to the objective such that a substantial portion of the fluorescence emitted by the sample region towards the objective reaches the objective without impinging on the mirror.

6. The fluorescence measurement instrument of claim 5 wherein the excitation means comprise a laser source.

7. The fluorescence measurement instrument of claim 5, wherein the light of the excitation means is reflected by the mirror substantially at right angles onto the sample, and the mirror is located in a path of emission light from the sample to the objective.

8. The fluorescent measurement instrument of claim 5, wherein said mirror reflects substantially all of the light incident thereon.

9. A fluorescence polarization measurement instrument comprising
   at least one sample region for receiving a sample;
   excitation means for producing light that is substantially linearly polarized along a first axis of polarization at the sample region;
   detection means that comprise an objective, a photodetector, and a polarization beam separator;
   wherein the photodetector provides a plurality of spatially distinct pixel regions;

the objective directs a beam of fluorescent light from the sample toward the polarization beam separator;

the polarization beam separator divides the beam of fluorescent light into two linearly polarized secondary beams, one with polarization axis oriented substantially parallel to the first axis of polarization and the other with polarization axis oriented substantially perpendicular to the first axis of polarization; and the secondary beams of fluorescent light are directed onto the spatially distinct pixel regions of the photodetector by the polarization beam separator.

10. The fluorescence polarization measurement instrument of claim 9, wherein the polarization beam separator is a planar element of doubly refractive material.

11. The fluorescence polarization measurement instrument of claim 10, wherein the polarization beam separator is made of calcite.

12. The fluorescence polarization measurement instrument of claim 10, wherein the polarization beam separator further comprises a second birefringent element that equalizes the optical path length between the two linearly polarized secondary beams.

13. A fluorescence polarization measurement instrument comprising:

at least one sample region for receiving a sample;

excitation means for producing light that is directed at the sample region to effect fluorescent emission of the sample and that is substantially linearly polarized along a first axis of polarization at the sample region;

detection means that comprise an objective, a plurality of independent detector regions, and a polarization beam separator;

wherein the plurality of independent detector regions comprises one of a unitary detector with multiple pixel regions and multiple detectors;

the objective collects the fluorescent emission from the sample region and directs the fluorescent emission in a beam toward the polarization beam separator;

the polarization beam separator divides the beam of fluorescent emission into two linearly polarized secondary beams, one with polarization axis oriented substantially parallel to the first axis of polarization and the other with polarization axis oriented substantially perpendicular to the first axis of polarization;

the linearly polarized secondary beams are directed by the polarization beam separator to separate detector regions; and said excitation means further provide switching means for changing the state of polarization of the excitation light at the sample region during a single fluorescence polarization measurement from a first orientation parallel to the first axis of polarization to a second orientation parallel to a second axis of polarization which is substantially perpendicular to the first axis of polarization.

14. The fluorescence polarization measurement instrument of claim 13 wherein the switching means are automated and do not require input to effect the changing of the state of polarization of the excitation light from the first orientation to the second orientation.

15. The fluorescence polarization measurement instrument of claim 14, wherein the switching means comprise a liquid crystal cell and associated drive circuitry.

16. The fluorescence polarization measurement instrument of claim 14, wherein the plural independent detector regions comprise a plurality of pixel regions on a unitary detector and the polarization beam separator comprises a planar element of doubly refractive material.

17. The fluorescence polarization measurement instrument of claim 15, wherein the plural independent detector regions comprise a plurality of pixel regions on a unitary detector and the polarization beam separator comprises a planar element of doubly refractive material.

18. The fluorescence polarization measurement instrument of claim 13, further comprising:

calculation means wherein the fluorescence polarization is calculated from four readings comprising an intensity of emission light of a first orientation generated from excitation light of a first orientation, an intensity of emission light of a second orientation generated from excitation light of a first orientation, an intensity of emission light of a first orientation generated from excitation light of a second orientation, an intensity of emission light of a second orientation generated from excitation light of a second orientation.

19. The fluorescence polarization measurement instrument of claim 14 which measures a plurality of sample regions simultaneously.

20. The fluorescence polarization measurement instrument of claim 19 where the plurality of sample regions comprise one of a linear array of points and a two-dimensional array of points.

21. The fluorescence polarization measurement instrument of claim 18 which measures a plurality of sample regions simultaneously.

22. The fluorescence polarization measurement instrument of claim 21, wherein the switching means comprise a liquid crystal cell and associated drive circuitry, and the plurality of independent detector regions comprise a plurality of pixel regions on a unitary detector and the polarization beam separator comprises a planar element of doubly refractive material.

23. The fluorescence polarization measurement instrument of claim 13, further comprising:

a means for monitoring the light substantially linearly polarized along a first axis of polarization which is produced by the excitation means, wherein said monitoring means provides feedback to adjust a polarization of the light produced by the excitation means.

24. The fluorescence polarization measurement instrument of claim 23, wherein the means for monitoring comprises:

a reflecting means for reflecting the light substantially linearly polarized along a first axis of polarization which is produced by the excitation means;

a polarization filtering means for receiving reflected light from the reflecting means, for only transmitting a component of the reflected light that is substantially linearly polarized along an axis of polarization to be monitored, and for not transmitting any other components; and a detector for receiving the transmitted component from the polarization filtering means and for detecting an intensity of said transmitted component.

25. The fluorescence polarization measurement instrument of claim 18, wherein the calculation means calculates the fluorescence polarization by the equation:

$$1000 * \frac{A - B + D - C}{A + B + D + C}$$

where A is the intensity of emission light of a first orientation generated from excitation light of a first orientation;

B is the intensity of emission light of a second orientation generated from excitation light of a first orientation;

C is the intensity of emission light of a first orientation generated from excitation light of a second orientation; and D is the intensity of emission light of a second orientation generated from excitation light of a second orientation.

26. The fluorescence polarization measurement instrument of claim 18, wherein the calculation means calculates the fluorescence polarization by the equation:

$$1000 * \frac{A - B + \gamma(D - C)}{A + B + \gamma(D + C)}$$

$$\text{where } \gamma = \left[\frac{A * B}{C * D}\right]^{\frac{1}{2}}$$

and where A is the intensity of emission light of a first orientation generated from excitation light of a first orientation;

B is the intensity of emission light of a second orientation generated from excitation light of a first orientation;

C is the intensity of emission light of a first orientation generated from excitation light of a second orientation; and D is the intensity of emission light of a second orientation generated from excitation light of a second orientation.

27. A fluorescence polarization measurement instrument comprising at least one sample region for receiving a sample;

excitation means for providing plural beams of excitation light that are directed at the at least one sample region to effect fluorescent emission and that are substantially linearly polarized along a first axis of polarization at the at least one sample region;

detection means that comprise an objective, plural independent detector regions, and a polarization beam separator;

wherein a principal ray of each of the plural beams of excitation light is substantially parallel to an optical axis of the objective.

28. The fluorescence polarization measurement instrument of claim 27, wherein the objective is telecentric at the at least one sample region.

29. A method of measuring fluorescence polarization of a sample, comprising illuminating the sample to effect fluorescence emission with a beam of excitation light that is linearly polarized along a first axis;

measuring the intensities of a first component of the fluorescence emission that is polarized along the first axis and a second component of the fluorescence emission that is polarized orthogonal to the first axis while the sample is illuminated with the beam of excitation light that is linearly polarized along the first axis;

switching the state of polarization of the beam of excitation light to a polarization state wherein said beam is linearly polarized along a second axis substantially orthogonal to the first axis;

measuring the intensities of a third component of fluorescence emission that is polarized along the first axis and a fourth component that is polarized orthogonal to the first axis while the sample is illuminated with the beam that is linearly polarized along the second axis; and calculating the fluorescence polarization of the sample based on the measurements of the intensities of the first, second, third and fourth components.

30. The method of measuring fluorescence polarization of claim 29, wherein the measurements of the intensities of the orthogonal components of fluorescence emission are made simultaneously.

31. The method of measuring fluorescence polarization of claim 29, wherein the fluorescence polarization is calculated using a self-calibrating algorithm that compensates for at least one of variations in intensity in the first beam, differing responsivity between measurements of the two orthogonal components of fluorescence emission, and photobleaching of the sample.

32. The method of measuring fluorescence polarization of claim 29, wherein the fluorescence polarization is calculated by the equation:

$$1000 * \frac{A - B + D - C}{A + B + D + C}$$

where A is the intensity of the first component;

B is the intensity of the second component;

C is the intensity of the third component; and

D is the intensity of the fourth component.

33. The method of measuring fluorescence polarization of claim 29, wherein the fluorescence polarization is calculated by the equation:

$$1000 * \frac{A - B + \gamma(D - C)}{A + B + \gamma(D + C)}$$

$$\text{where } \gamma = \left[\frac{A * B}{C * D}\right]^{\frac{1}{2}}$$

and where A is the intensity of the first component;

B is the intensity of the second component;

C is the intensity of the third component; and

D is the intensity of the fourth component.

34. A method of measuring fluorescence of a sample, comprising:

providing an excitation beam of light;

positioning a mirror between the sample and an objective which collects the fluorescence emission from the sample;

reflecting the excitation beam of light from the mirror onto the sample to effect fluorescence emission, the mirror being small in size relative to the objective such that a substantial portion of the fluorescence emitted by the sample reaches the objective without impinging on the mirror; and directing the fluorescence emission collected by the objective to a detection means for measurement.

35. The method of measuring fluorescence of claim 34, further comprising the step of:

selecting the size of the mirror such that the mirror does not completely block the fluorescence emission from collection by the objective.

36. The method of measuring fluorescence of claim 34, further including the steps of polarizing the excitation beam of light along a first linear polarization axis, analyzing the state of polarization of the fluorescence emission and determining the degree of fluorescence polarization of the sample.

37. The method of measuring fluorescence of claim 34, wherein all optical filters through which emission light travels in passing from sample to detection means are oriented substantially normal to an optical axis.

38. The method of claim 37, further including the steps of analyzing the state of polarization of the fluorescence emission and determining the degree of fluorescence polarization of the sample.

39. The method of claim 38, wherein the sample exhibits a maximum emission wavelength that is less than 20 nm from the maximum excitation wavelength.

40. The method of claim 38, where the sample comprises a Bodipy probe.

41. The method of claim 38 where the sample comprises an Alexa probe.

42. The method of claim 38, further including the steps of:
separating the emission light into a first component which is polarized along a first polarization axis and a second component which is polarized along a second polarization axis orthogonal to the first linear polarization axis; and
measuring both components simultaneously.

43. The method of claim 42, further including the steps of:
rotating the plane of polarization of the excitation beam from the first polarization axis to a second polarization axis substantially perpendicular to the first axis;
separating the emission light into a third component which is polarized along the first polarization axis and a fourth component which is polarized along the second polarization axis; and
measuring both components simultaneously while the excitation beam is polarized along said second axis.

44. The method of claim 42 further including the step of calculating the fluorescence polarization from the measurements of the two polarized components of the emission light.

45. The method of claim 43 further including the step of calculating the fluorescence polarization from the four measurements comprising the intensity of the two polarized components of the emission light when said excitation beam is polarized along said first polarization axis, and when said excitation beam is polarized along said second polarization axis.

46. The method of claim 45 where the fluorescence polarization is calculated using an algorithm that compensates for one of variations in intensity in the first beam, differing responsivity between measurements of the two components of emission light, and photobleaching of the sample.

47. The method of claim 45 wherein the sample exhibits a separation of 20 nm or less between the wavelength of peak absorption and the wavelength of peak emission.

48. The method of claim 47 where the sample comprises a Bodipy probe.

49. The method of claim 47 where the sample comprises an Alexa probe.

50. The method of measuring fluorescence claim 34, wherein the light of the excitation means is reflected by the mirror substantially at right angles onto the sample, and the mirror is located substantially in a path of emission light from the sample to the objective.

51. The method of claim 45, wherein the step of calculating the fluorescence polarization uses the equation:

$$1000 * \frac{A - B + D - C}{A + B + D + C}$$

where A is an intensity of the first component;
B is an intensity of the second component;
C is the intensity of the third component; and
D is the intensity of the fourth component.

52. The method of claim 45, wherein the step of calculating the fluorescence polarization uses the equation:

$$1000 * \frac{A - B + \gamma(D - C)}{A + B + \gamma(D + C)}$$

$$\text{where } \gamma = \left[\frac{A * B}{C * D}\right]^{\frac{1}{2}}$$

and where A is the intensity of the first component;
B is the intensity of the second component;
C is the intensity of the third component; and
D is the intensity of the fourth component.

53. The method of measuring fluorescence of claim 34, further comprising the step of:
selecting the size of the mirror such that the mirror does not substantially block the fluorescence emission from collection by the objective.

54. A method of determining the integrity of a sample for fluorescence measurement, comprising
providing a sample;
providing a beam of excitation light that is directed toward the sample;
collecting emission light from the sample with an objective; and
recording an image of said sample on a detector, said image being recorded with multiple independent pixel regions arranged in a two-dimensional array; wherein the size of the pixel regions is chosen so the recorded image is comprised of enough pixel regions to produce a spatial distribution of intensity readings;
recording a spatial distribution of detector intensity readings for pixel regions within the recorded image; and
determining a measurement integrity of the sample based on a shape and uniformity of the spatial distribution of detector intensity readings, where an abnormal distribution indicates that the sample is suspect.

55. The method of claim 54 further including the steps of polarizing the excitation light along a first linear polarization axis, analyzing the state of polarization of the emission light and determining the degree of fluorescence polarization.

56. A method for taking a fluorescence polarization measurement comprising:
exciting a sample with excitation light of a first polarization;
separating resulting emission light from the sample into first and second orthogonally polarized components;
detecting intensities of the first and second components;
exciting the sample with excitation light of a second polarization orthogonal to said first polarization;
separating resulting emission light from the sample into third and fourth orthogonally polarized components wherein said third component has the same polarization as one of said first and second components and said fourth component has the same polarization as the other of said first and second components;

detecting intensities of the third and fourth components; and calculating the fluorescence polarization using a self-calibrating equation that compensates for at least one of variations in intensity of the excitation light of the first polarization, differing responsivity between measurements of the two orthogonal components of fluorescence emission, and photobleaching of the sample.

57. The method of claim 56, wherein the step of calculating the fluorescence polarization uses the self-calibrating equation:

$$1000 * \frac{A - B + D - C}{A + B + D + C}$$

where A is an intensity of the first component;
B is an intensity of the second component;
C is the intensity of the third component; and
D is the intensity of the fourth component.

58. The method of claim 56, wherein the step of calculating the fluorescence polarization uses the self-calibrating equation:

$$1000 * \frac{A - B + \gamma(D - C)}{A + B + \gamma(D + C)}$$

where $\gamma = \left[\frac{A * B}{C * D}\right]^{\frac{1}{2}}$ and where A is the intensity of the first component;
B is the intensity of the second component;
C is the intensity of the third component; and
D is the intensity of the fourth component.

59. The method of claim 56, wherein said step of detecting the intensity of said first and second components comprises simultaneously detecting the intensity of said first and second components and wherein the step or detecting the intensity of said third and fourth components comprises simultaneously measuring the intensity of said third and fourth components.

60. A method of determining the integrity of a sample for fluorescence measurement, comprising the steps of:

selecting a plurality of pixel regions on a detector, each of said plurality of pixel regions covering an area on the detector where emission light from a single sample will impinge the detector;

selecting a pixel group size within each pixel region, each pixel group comprising a square of one or more pixels and producing a single reading, each pixel region comprising a plurality of pixel groups;

directing excitation beams of light towards a plurality of samples;

collecting emission light from the plurality of samples with an objective;

directing the collected emission light of each of the plurality of samples as an image on a pixel region on the detector;

detecting, for each image, intensity readings of the plurality of pixel groups comprising the pixel region on the detector corresponding to the image;

determining a spatial distribution of intensity readings for each image; and determining the integrity of each of the plurality of samples by determining if a spatial distribution of intensity readings of an image of said each sample is uniform within its respective pixel region, wherein a uniform distribution indicates a sample with integrity;

wherein the pixel group size is chosen so that a non-uniform distribution will be detected.

\* \* \* \* \*